(12) United States Patent
Hout et al.

(10) Patent No.: US 9,428,812 B2
(45) Date of Patent: Aug. 30, 2016

(54) KIT COMPRISING PRIMERS FOR AMPLIFYING ALK KINASE DOMAIN NUCLEIC ACIDS

(71) Applicant: INSIGHT GENETICS, INC., Nashville, TN (US)

(72) Inventors: David R. Hout, Nashville, TN (US); Rachel Skelton, Kingston, TN (US); John Handshoe, Bethoage, TN (US); Kasey Lawrence, Mount Juliet, TN (US); Brock Schweitzer, Nashville, TN (US)

(73) Assignee: Insight Genetics, Inc., Nashville, TN (US)

( * ) Notice: Subject to any disclaimer, the term of this patent is extended or adjusted under 35 U.S.C. 154(b) by 0 days.

(21) Appl. No.: 14/304,543

(22) Filed: Jun. 13, 2014

(65) Prior Publication Data
US 2015/0307944 A1    Oct. 29, 2015

Related U.S. Application Data

(60) Provisional application No. 61/985,023, filed on Apr. 28, 2014.

(51) Int. Cl.
| | | |
|---|---|---|
| *C12P 19/34* | (2006.01) | |
| *C07H 21/04* | (2006.01) | |
| *C12Q 1/68* | (2006.01) | |

(52) U.S. Cl.
CPC ....... *C12Q 1/6886* (2013.01); *C12Q 2600/136* (2013.01); *C12Q 2600/156* (2013.01); *C12Q 2600/158* (2013.01)

(58) Field of Classification Search
USPC ...................................................... 536/24.33
See application file for complete search history.

(56) References Cited

U.S. PATENT DOCUMENTS

| 8,383,793 B2 * | 2/2013 | Morris et al. ................. 536/23.1 |
| 2012/0208713 A1 * | 8/2012 | Nickols et al. .................... 506/9 |
| 2013/0203810 A1 * | 8/2013 | Mano et al. ................... 514/318 |

OTHER PUBLICATIONS

U.S. Office Action issued in related patent application, dated Feb. 3, 2015.
U.S. Office Action issued in related patent application, dated Oct. 11, 2013.
U.S. Office Action issued in related patent application, dated May 3, 2013.
Translation of the Japanese Office Action from the related application; Sep. 8, 2014.
Translation of the Russian Office Action from the related application; Nov. 14, 2014.
International Search Report from the related application; Nov. 19, 2010.
Office Action from related Mexican Application; Dec. 3, 2014.
Office Action from the related Mexican Application; Jun. 28, 2013.
Office Action from the related Mexican Application; Mar. 19, 2014.
Examination Report from the related Australian Application; Sep. 12, 2013.
Examination Report from the related European Application; Jun. 25, 2013.
Office Action from related Chinese Application; Jun. 28, 2013.
Hacia JG. Resequencing and mutational analysis using oligonucleotide microarrays. Nat Genet 1999;21(1 Suppl):42-7.
Hovig E, Smith-Sorensen B, Brogger A, Borresen AL. Constant denaturant gel electrophoresis, a modification of denaturing gradient gel . . . ; Mutat Res 1991;262(1):63-71.
Labeit S, Lehrach H, Goody RS. A new method of DNA sequencing using deoxynucleoside alpha-thiotriphosphates. Dna 1986;5(2):173-7.
Labeit S, Lehrach H, Goody RS. DNA sequencing using alpha-thiodeoxynucleotides. Methods Enzymol 1987;155:166-77.
Lamant L et al., Genes Chromosomes Cancer. Aug. 2003;37(4):427-32.
Li R, Morris SW., Med Res Rev. May 2008;28(3):372-412.
Lu AL, Hsu IC. Detection of single DNA base mutations with mismatch repair enzymes. Genomics 1992;14(2):249-55.
Mano H., Cancer Sci. Dec. 2008;99(12):2349-55.
Myers RM, Larin Z, Maniatis T. Detection of single base substitutions by ribonuclease cleavage at mismatches in RNA:DNA duplexes. Science 1985;230(4731):1242-6.
Nagamine CM, Chan K, Lau YF. A PCR artifact: generation of heteroduplexes. Am J Hum Genet 1989;45(2):337-9.
Nakamaye KL, Gish G, Eckstein F, Vosberg HP. Direct sequencing of polymerase chain reaction amplified DNA fragments through . . . ; Nucleic Acids Res 1988;16(21):9947-59.
Novack DF, Casna NJ, Fischer SG, Ford JP. Detection of single base-pair mismatches in DNA by chemical modification followed by . . . ; Proc Natl Acad Sci U S A 1986;83(3):586-90.
Oldenburg MC, Siebert M. New Cleavase Fragment Length Polymorphism method improves the mutation detection assay. Biotechniques 2000;28(2):351-7.
Orita M, Suzuki Y, Sekiya T, Hayashi K. Rapid and sensitive detection of point mutations and DNA polymorphisms . . . ; Genomics 1989;5(4):874-9.
Pincas H, Pingle MR, Huang J, et al. High sensitivity EndoV mutation scanning through real-time ligase proofreading. Nucleic Acids Res 2004;32(19):e148.
Porter KW, Briley JD, Shaw BR. Direct PCR sequencing with boronated nucleotides. Nucleic Acids Res 1997;25(8):1611-7.
Rudzki Z et al., Pol J Pathol. 2005;56(1):37-45.
Takeuchi K et al., Clin Cancer Res. May 1, 2009;15(9):3143-9.
Winter E, Yamamoto F, Almoguera C, Perucho M. A method to detect and characterize point mutations in transcribed genes . . . ; Proc Natl Acad Sci U S A 1985;82(22):7575-9.
Xiao W, Oefner PJ. Denaturing high-performance liquid chromatography: A review. Hum Mutat 2001;17(6):439-74.

(Continued)

*Primary Examiner* — Kenneth Horlick
(74) *Attorney, Agent, or Firm* — Smith, Gambrell & Russell

(57) ABSTRACT

Disclosed are methods and kits for detecting the presence of a cancer in a subject and assessing the efficacy of treatments for the same. The disclosed method use reverse transcription polymerase chain reaction (RT-PCR) techniques to detect the presence of point mutations, truncations, or fusions of anaplastic lymphoma kinase.

8 Claims, 4 Drawing Sheets

(56) References Cited

OTHER PUBLICATIONS

Youil R, Kemper B, Cotton RG. Detection of 81 of 81 known mouse beta-globin promoter mutations with T4 endonuclease VII—the EMC method. Genomics 1996;32:431-5.

Lamant, et al, Expression of the ALK Tyrosine Kinase Gene in Neuroblastoma; American Journal of Pathology, May 2000, 156, No. 5; 1711-1721.

Lawrence, et al.; American J of Pathology 2000; 157:377.

Mosse, et al.; Nature 2008; 455.

Catalog of Somatic Mutations in Cancer; R401Q, Sanger Institute, 2006.

Catalog of Somatic Mutations in Cancer; A877S; Sanger Institute, 2006.

Lu, et al; Clinical Cancer Research, 2000, 6:3166-3171.

Soda, et al; Nature 2007: 448:561-567.

* cited by examiner

| Translocation | Frequency in ALK+ Lymphomas | Occurrence in IMT | Localization |
|---|---|---|---|
| t(2;5)(p23;q35) | ~75% | – | N/C |
| t(1;2)(q25;p23) | ~18% | + | C |
| inv(2)(p23q35) | ~2% | – | C |
| t(2;17)(p23;q23) | ~2% | + | C |
| t(2;3)(p23;q21) | ~1% | – | C |
| t(2;3)(p23;q21) | ~1% | – | C |
| t(2;19)(p23;p13.1) | <1% | + | C |
| t(2;X)(p23;q11-12) | <1% | – | CM |
| t(2;2)(p23;q11-13)? or inv(2)(p23q11-13)? | – | + | NM |
| inv(2)(p21p23) | – | – | C |

Figure 1

SEQUENCE LISTING

<160> NUMBER OF SEQ ID NOS: 97

<210> SEQ ID NO 1
<211> LENGTH: 1620
<212> TYPE: PRT
<213> ORGANISM: Homo sapiens

<400> SEQUENCE: 1

Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Pro Ser Leu Phe
    50                  55                  60

Arg Val Tyr Ala Arg Asp Leu Leu Leu Pro Pro Ser Ser Ser Glu Leu

```
              65                  70                  75                  80
Lys Ala Gly Arg Pro Glu Ala Arg Gly Ser Leu Ala Leu Asp Cys Ala
                    85                  90                  95

Pro Leu Leu Arg Leu Leu Gly Pro Ala Pro Gly Val Ser Trp Thr Ala
                100                 105                 110

Gly Ser Pro Ala Pro Ala Glu Ala Arg Thr Leu Ser Arg Val Leu Lys
                115                 120                 125

Gly Gly Ser Val Arg Lys Leu Arg Arg Ala Lys Gln Leu Val Leu Glu
            130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
                180                 185                 190

Lys Lys Ala Ser Glu Val Gly Arg Glu Gly Arg Leu Ser Ala Ala Ile
            195                 200                 205

Arg Ala Ser Gln Pro Arg Leu Leu Phe Gln Ile Phe Gly Thr Gly His
        210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
                260                 265                 270

Glu Leu Glu Tyr Ser Pro Pro Leu His Asp Leu Arg Asn Gln Ser Trp
            275                 280                 285

Ser Trp Arg Arg Ile Pro Ser Glu Glu Ala Ser Gln Met Asp Leu Leu
        290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Glu His Cys Thr Leu Ala Val Ser Val His
                340                 345                 350

Arg His Leu Gln Pro Ser Gly Arg Tyr Ile Ala Gln Leu Leu Pro His
            355                 360                 365

Asn Glu Ala Ala Arg Glu Ile Leu Leu Met Pro Thr Pro Gly Lys His
370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
                420                 425                 430

Ser Lys Met Ala Leu Gln Ser Ser Phe Thr Cys Trp Asn Gly Thr Val
            435                 440                 445

Leu Gln Leu Gly Gln Ala Cys Asp Phe His Gln Asp Cys Ala Gln Gly
        450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495
```

```
His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
            515                 520                 525

Ser Glu Ser Ala Thr Val Thr Ser Ala Thr Phe Pro Ala Pro Ile Lys
            530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
            580                 585                 590

Trp Gln Trp Met Val Leu Pro Leu Leu Asp Val Ser Asp Arg Phe Trp
            595                 600                 605

Leu Gln Met Val Ala Trp Trp Gly Gln Gly Ser Arg Ala Ile Val Ala
            610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
            660                 665                 670

Gln Thr Pro Ile Phe Asp Pro Thr Val His Trp Leu Phe Thr Thr Cys
            675                 680                 685

Gly Ala Ser Gly Pro His Gly Pro Thr Gln Ala Gln Cys Asn Asn Ala
            690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
                725                 730                 735

Ser Gly Tyr Gly Ala Ala Gly Gly Lys Gly Gly Lys Asn Thr Met Met
            740                 745                 750

Arg Ser His Gly Val Ser Val Leu Gly Ile Phe Asn Leu Glu Lys Asp
            755                 760                 765

Asp Met Leu Tyr Ile Leu Val Gly Gln Gln Gly Glu Asp Ala Cys Pro
            770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                805                 810                 815

Gly Gly Gly Gly Gly Gly Ala Thr Tyr Val Phe Lys Met Lys Asp
            820                 825                 830

Gly Val Pro Val Pro Leu Ile Ile Ala Ala Gly Gly Gly Arg Ala
            835                 840                 845

Tyr Gly Ala Lys Thr Asp Thr Phe His Pro Glu Arg Leu Glu Asn Asn
            850                 855                 860

Ser Ser Val Leu Gly Leu Asn Gly Asn Ser Gly Ala Ala Gly Gly Gly
865                 870                 875                 880

Gly Gly Trp Asn Asp Asn Thr Ser Leu Leu Trp Ala Gly Lys Ser Leu
                885                 890                 895

Gln Glu Gly Ala Thr Gly Gly His Ser Cys Pro Gln Ala Met Lys Lys
            900                 905                 910
```

-continued

```
Trp Gly Trp Glu Thr Arg Gly Gly Phe Gly Gly Gly Gly Gly Cys
            915                 920                 925

Ser Ser Gly Gly Gly Gly Gly Tyr Ile Gly Gly Asn Ala Ala Ser
    930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
            965                 970                 975

Gly Glu Val Asn Ile Lys His Tyr Leu Asn Cys Ser His Cys Glu Val
                980                 985                 990

Asp Glu Cys His Met Asp Pro Glu  Ser His Lys Val Ile Cys Phe Cys
            995                 1000                1005

Asp His  Gly Thr Val Leu Ala  Glu Asp Gly Val Ser  Cys Ile Val
    1010                1015                 1020

Ser Pro  Thr Pro Glu Pro His  Leu Pro Leu Ser Leu  Ile Leu Ser
    1025                1030                 1035

Val Val  Thr Ser Ala Leu Val  Ala Ala Leu Val Leu  Ala Phe Ser
    1040                1045                 1050

Gly Ile  Met Ile Val Tyr Arg  Arg Lys His Gln Glu  Leu Gln Ala
    1055                1060                 1065

Met Gln  Met Glu Leu Gln Ser  Pro Glu Tyr Lys Leu  Ser Lys Leu
    1070                1075                 1080

Arg Thr  Ser Thr Ile Met Thr  Asp Tyr Asn Pro Asn  Tyr Cys Phe
    1085                1090                 1095

Ala Gly  Lys Thr Ser Ser Ile  Ser Asp Leu Lys Glu  Val Pro Arg
    1100                1105                 1110

Lys Asn  Ile Thr Leu Ile Arg  Gly Leu Gly His Gly  Ala Phe Gly
    1115                1120                 1125

Glu Val  Tyr Glu Gly Gln Val  Ser Gly Met Pro Asn  Asp Pro Ser
    1130                1135                 1140

Pro Leu  Gln Val Ala Val Lys  Thr Leu Pro Glu Val  Cys Ser Glu
    1145                1150                 1155

Gln Asp  Glu Leu Asp Phe Leu  Met Glu Ala Leu Ile  Ile Ser Lys
    1160                1165                 1170

Phe Asn  His Gln Asn Ile Val  Arg Cys Ile Gly Val  Ser Leu Gln
    1175                1180                 1185

Ser Leu  Pro Arg Phe Ile Leu  Leu Glu Leu Met Ala  Gly Gly Asp
    1190                1195                 1200

Leu Lys  Ser Phe Leu Arg Glu  Thr Arg Pro Arg Pro  Ser Gln Pro
    1205                1210                 1215

Ser Ser  Leu Ala Met Leu Asp  Leu Leu His Val Ala  Arg Asp Ile
    1220                1225                 1230

Ala Cys  Gly Cys Gln Tyr Leu  Glu Glu Asn His Phe  Ile His Arg
    1235                1240                 1245

Asp Ile  Ala Ala Arg Asn Cys  Leu Leu Thr Cys Pro  Gly Pro Gly
    1250                1255                 1260

Arg Val  Ala Lys Ile Gly Asp  Phe Gly Met Ala Arg  Asp Ile Tyr
    1265                1270                 1275

Arg Ala  Ser Tyr Tyr Arg Lys  Gly Gly Cys Ala Met  Leu Pro Val
    1280                1285                 1290

Lys Trp  Met Pro Pro Glu Ala  Phe Met Glu Gly Ile  Phe Thr Ser
    1295                1300                 1305

Lys Thr  Asp Thr Trp Ser Phe  Gly Val Leu Leu Trp  Glu Ile Phe
```

-continued

```
            1310                1315                1320
Ser Leu Gly Tyr Met Pro Tyr Pro Ser Lys Ser Asn Gln Glu Val
        1325                1330                1335

Leu Glu Phe Val Thr Ser Gly Gly Arg Met Asp Pro Pro Lys Asn
        1340                1345                1350

Cys Pro Gly Pro Val Tyr Arg Ile Met Thr Gln Cys Trp Gln His
        1355                1360                1365

Gln Pro Glu Asp Arg Pro Asn Phe Ala Ile Ile Leu Glu Arg Ile
        1370                1375                1380

Glu Tyr Cys Thr Gln Asp Pro Asp Val Ile Asn Thr Ala Leu Pro
        1385                1390                1395

Ile Glu Tyr Gly Pro Leu Val Glu Glu Glu Lys Val Pro Val
        1400                1405                1410

Arg Pro Lys Asp Pro Glu Gly Val Pro Pro Leu Leu Val Ser Gln
        1415                1420                1425

Gln Ala Lys Arg Glu Glu Arg Ser Pro Ala Ala Pro Pro Pro
        1430                1435                1440

Leu Pro Thr Thr Ser Ser Gly Lys Ala Ala Lys Lys Pro Thr Ala
        1445                1450                1455

Ala Glu Ile Ser Val Arg Val Pro Arg Gly Pro Ala Val Glu Gly
        1460                1465                1470

Gly His Val Asn Met Ala Phe Ser Gln Ser Asn Pro Pro Ser Glu
        1475                1480                1485

Leu His Lys Val His Gly Ser Arg Asn Lys Pro Thr Ser Leu Trp
        1490                1495                1500

Asn Pro Thr Tyr Gly Ser Trp Phe Thr Glu Lys Pro Thr Lys Lys
        1505                1510                1515

Asn Asn Pro Ile Ala Lys Lys Glu Pro His Asp Arg Gly Asn Leu
        1520                1525                1530

Gly Leu Glu Gly Ser Cys Thr Val Pro Pro Asn Val Ala Thr Gly
        1535                1540                1545

Arg Leu Pro Gly Ala Ser Leu Leu Leu Glu Pro Ser Ser Leu Thr
        1550                1555                1560

Ala Asn Met Lys Glu Val Pro Leu Phe Arg Leu Arg His Phe Pro
        1565                1570                1575

Cys Gly Asn Val Asn Tyr Gly Tyr Gln Gln Gln Gly Leu Pro Leu
        1580                1585                1590

Glu Ala Ala Thr Ala Pro Gly Ala Gly His Tyr Glu Asp Thr Ile
        1595                1600                1605

Leu Lys Ser Lys Asn Ser Met Asn Gln Pro Gly Pro
        1610                1615                1620
```

<210> SEQ ID NO 2
<211> LENGTH: 58
<212> TYPE: DNA
<213> ORGANISM: Artificial Sequence
<220> FEATURE:
<223> OTHER INFORMATION: Synthetic construct

<400> SEQUENCE: 2
ccgcgccact tcatccaccg agacattgcg cgcggggaca ggtcaagagg cagtttct        58

<210> SEQ ID NO 3
<211> LENGTH: 23
<212> TYPE: DNA
<213> ORGANISM: Artificial Sequence
<220> FEATURE:
<223> OTHER INFORMATION: Synthetic construct

<400> SEQUENCE: 3
ttctgcacgt ggctcgggac att                                               23

<210> SEQ ID NO 4
<211> LENGTH: 48
<212> TYPE: DNA
<213> ORGANISM: Artificial Sequence
<220> FEATURE:
<223> OTHER INFORMATION: Synthetic construct

<400> SEQUENCE: 4
acgcgcctac gggaacctcc tggcgcgtcg gttgcactcc ctcaggta                    48

<210> SEQ ID NO 5
<211> LENGTH: 19
<212> TYPE: DNA
<213> ORGANISM: Artificial Sequence
<220> FEATURE:
<223> OTHER INFORMATION: Synthetic construct

<400> SEQUENCE: 5
gcagctcctt ggggtctgc                                                    19

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 6
tcgtcctgtt cagagcacac ttca                                              24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 7
actactgctt tgctggcaag acct                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 8
tgttcaagat cgcctgtcag ctct                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 9
tctgtacagc caacggtttc cctt                                        24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 10
gagagtgctt tggagcttgt ctgt                                        24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 11
ttccttcatc agtccactgg gcat                                        24

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 12
gcgtttctct cttcccactc                                             20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 13
gcctgaagac ctggaattgg                                             20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 14
ggaaggtgaa ggtcggagtc                                             20

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 15
ccagccgaag gagaaggg                                                 18

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 16
taccgcattc cgtccactc                                                19

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 17
cggcagtcag gcatttgg                                                 18

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 18
ctctccttcg tggcatctat g                                             21

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 19
ggacatccgc cataacaagg                                               20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 20
agacggtcat agccaaggag                                               20

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 21
acgcaatggc ttcaaggtta c                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 22
ggcatagcga ccttcaatac c                                              21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 23
ctgacataag tggatgcgaa tc                                             22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 24
gctgatgatc ttgaggctgt tg                                             22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 25
agggaagttt gcgaatcaga ag                                             22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 26
gctcctcatc aatcaccatc tg                                             22

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 27
ccaccacgaa gtctcaacac                                                20

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 28
ggtctccttg aactcaatct cc                                              22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 29
acaacctctt caacacaacc tg                                              22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 30
gcagaggagt cagacacatt g                                               21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 31
cgctggtatt gtcctcttca c                                               21

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 32
ggtcttgcca gcaaagcagt agtt                                            24

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 33
tgtgctaaag gcggctttgg ctgatgtt                                        28

<210> SEQ ID NO 34
<211> LENGTH: 43
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 34
tcactgagaa aagaagaaga acaagctaca gagacacaac cca          43

<210> SEQ ID NO 35
<211> LENGTH: 39
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 35
tacatcacac accttgactg gtccccagac aacaagtat              39

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 36
tattgtactt gtaccgccgg aagcaccag                         29

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 37
tgtgctaaag gcggctttgg ctgatgtt                          28

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 38
aatcactgtg ctaaaggcgg ctttggct                          28

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 39
aaacagccaa gtgtaccgcc ggaag                             25

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 40
tatgctggat gagccctgag tacaagctga                                    30

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 41
agagatatgc tggatgagcc ctgagt                                        26

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 42
ggaggatatg gagatccagg gaggcttcct gtaggaa                            37

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 43
tgtgtagtgc ttcaagggcc aggct                                         25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 44
tgtgtagtgc ttcaagggcc aggct                                         25

<210> SEQ ID NO 45
<211> LENGTH: 29
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 45
tgggaaagga cctaaaggaa gtggcctgt                                     29

<210> SEQ ID NO 46

```
<211> LENGTH: 23
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 46
ttgctcagct tgtactcagg gct                                            23

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 47
agggcttcca tgaggaaatc cagt                                           24

<210> SEQ ID NO 48
<211> LENGTH: 37
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 48
ctgaaagaga aatagagcac caggagctgc aagccat                             37

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 49
agaaatagag caccaggagc tgcaagccat                                     30

<210> SEQ ID NO 50
<211> LENGTH: 43
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 50
ctatcagcaa gaagtagatc gcataaagga agcagtcagg tca                      43

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 51
atggccagaa gagggcattc tgcacagatt                                     30

<210> SEQ ID NO 52
<211> LENGTH: 28
```

```
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 52
tgacagctcg aatctcccag ctggagat                                        28

<210> SEQ ID NO 53
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 53
tggccttgga aatggcagag ctgaca                                          26

<210> SEQ ID NO 54
<211> LENGTH: 30
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 54
cgtgctgaat ttgcagagag aacggttgca                                      30

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 55
aaagaggctg agacccgtgc tgaatttgca                                      30

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 56
aatgtctgta cagccaacgg tttcccttgg                                      30

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 57
tcgtcctgtt cagagcacac ttca                                            24

<210> SEQ ID NO 58
<211> LENGTH: 25
<212> TYPE: DNA
```

<213> ORGANISM: Artificial Sequence
<220> FEATURE:
<223> OTHER INFORMATION: Description of Artificial Sequence: Note = Synthetic Construct

<400> SEQUENCE: 58
aggtcttgcc agcaaagcag tagtt    25

<210> SEQ ID NO 59
<211> LENGTH: 27
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 59
aaggttgaag tgtggttcag ggccagt    27

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 60
atgtcacatg gaccctgaaa gccacaaggt    30

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 61
tcggttctag ggctaaacgg caat    24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 62
agcagatatg gaaggtgcac tgga    24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence: Note = Synthetic Construct

<400> SEQUENCE: 63
tctcaagtaa agtgtaccgc cgga    24

<210> SEQ ID NO 64
<211> LENGTH: 26
<212> TYPE: DNA
<213> ORGANISM: Artificial Sequence

```
<220> FEATURE:
<223> OTHER INFORMATION: Description of Artificial Sequence: Note =
      Synthetic Construct

<400> SEQUENCE: 64
acctcgacca tcatgaccga ctacaa                                            26

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 65
agatatgctg gatgagccct gagt                                              24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 66
caatcatgat gccggagaaa gcca                                              24

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 67
gaagtggcct gtgtagtgct tcaa                                              24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 68
aaaggaagtg gcctgtgtag tgct                                              24

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 69
agaaatagag caccaggagc tgcaag                                            26

<210> SEQ ID NO 70
<211> LENGTH: 24
<212> TYPE: DNA
<213> ORGANISM: Artificial Sequence
<220> FEATURE:
```

```
<223> OTHER INFORMATION: Description of Artificial Sequence: Note =
      Synthetic Construct

<400> SEQUENCE: 70
gcagaggcaa tgaattacga aggc                                           24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 71
aaactgaaag aggctgagac ccgt                                           24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 72
tcaggaacag ctggccttgg aaat                                           24

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 73
ttgtttatgt gtaccgccgg aagc                                           24

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 74
tgtaccgccg gaagcaccag gag                                            23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 75
tgtaccgccg gaagcaccag gag                                            23

<210> SEQ ID NO 76
<211> LENGTH: 26
<212> TYPE: DNA
<213> ORGANISM: Artificial Sequence
<220> FEATURE:
<223> OTHER INFORMATION: Description of Artificial Sequence: Note =
```

Synthetic Construct

<400> SEQUENCE: 76
gatgaaatca ctgtgctaaa ggcggc                                              26

<210> SEQ ID NO 77
<211> LENGTH: 27
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 77
gcagacaagc ataaagatgt catcatc                                             27

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 78
ccacacctgg gaaaggacct aaagg                                               25

<210> SEQ ID NO 79
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 79
tgccatgccc tatttcatcc aggt                                                24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 80
gcagaggcaa tgaattacga aggc                                                24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 81
accctgaaag ccacaaggtc atct                                                24

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 82
acgcaatggc ttcaaggtta c                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 83
cgctggtatt gtcctcttca c                                              21

<210> SEQ ID NO 84
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 84
aggatggcgt ctcctgcatt gtgtca                                         26

<210> SEQ ID NO 85
<211> LENGTH: 25
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 85
tgtatgaagg ccaggtgtcc ggaat                                          25

<210> SEQ ID NO 86
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 86
tcaggcacca gggaagaccc taattt                                         26

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 87
aactcagacc caggtttgga acctga                                         26

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 88
tccttcgtgg catctatgct tacggt                                        26

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 89
ctgaaagcca caaggtcatc tgct                                          24

<210> SEQ ID NO 90
<211> LENGTH: 26
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 90
aactactgct ttgctggcaa gacctc                                        26

<210> SEQ ID NO 91
<211> LENGTH: 24
<212> TYPE: DNA
<213> ORGANISM: Artificial Sequence
<220> FEATURE:
<223> OTHER INFORMATION: Synthetic construct

<400> SEQUENCE: 91
tcgtcctgtt cagagcacac ttca                                          24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 92
tgcaaagaag ggactggacc cata                                          24

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 93
ttgtcctctt cacagatgca gcct                                          24

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 94

```
agaccagaca gtcatagcca agga                                              24

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 95
aaggcagatg tggagttgct gtct                                              24

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 96
tataacagag aacatggcgg ccca                                              24

<210> SEQ ID NO 97
<211> LENGTH: 24
<212> TYPE: DNA
<213> ORGANISM: Artificial Sequence
<220> FEATURE:
<223> OTHER INFORMATION: Description of Artificial Sequence: Note =
      Synthetic Construct

<400> SEQUENCE: 97
tgcatctcgt gatcgcaaac gcta                                              24
```

KIT COMPRISING PRIMERS FOR AMPLIFYING ALK KINASE DOMAIN NUCLEIC ACIDS

This application is a continuation-in-part of and claims priority to U.S. application Ser. No. 13/320,303, filed on May 17, 2010 which claims the benefit of U.S. Provisional Application No. 61/178,937, filed on May 15, 2009. The application claims the benefit of U.S. Provisional Application No. 61/985,023, filed on Apr. 28, 2014.

BACKGROUND

Mutations of anaplastic lymphoma kinase (ALK) are thought to be involved in the development of subsets of numerous cancers including i) non-small cell lung carcinoma; ii) diffuse large B-cell lymphoma; iii) esophageal squamous cell carcinoma; iv) anaplastic large-cell lymphoma; v) neuroblastoma (a childhood cancer that arises from the developing peripheral nervous system); and vi) the sarcomas known as inflammatory myofibroblastic tumors (IMTs). Patient outcomes with many of these malignancies are poor, due in part to the late detection of the cancers because of the lack of efficient clinical diagnostic methods. Early detection and diagnosis of ALK-mediated cancers dramatically increases survival rates within the patient population; as an example, early detection of ALK-positive anaplastic large-cell lymphoma can result in survival rates of up to 83% whereas late detection is associated in some instances with survival of only 50% of the patient population. A technology that would allow for earlier detection of these cancers could greatly facilitate the medical management of the patients suffering from them, helping ultimately to improve their treatment outcomes. Both preclinical and early clinical data indicate that only those cancers that express activating ALK mutations that drive their development and progression exhibit robust antitumor responses to ALK small-molecule inhibitors.

BRIEF SUMMARY

The methods and compositions disclosed herein relate to the field of detection or diagnosis of the presence of a disease or condition such as cancer; assessing the susceptibility or risk for a disease or condition such as cancer; the monitoring disease progression for a disease such as cancer; and the determination of susceptibility or resistance to therapeutic treatment of a disease such as cancer, wherein the disease or condition is a cancer associated with a nucleic acid variation, truncation, or gene fusion of the ALK gene. It is understood and herein contemplated that the methods disclosed herein allow for rapid and sensitive detection of rare mutations (i.e., nucleotide variations that are low in number) including mutations comprising polypeptide fusions in the presence of excess normal DNA as well as the detection of rare truncations and aberrant over-expression of wildtype genes.

In accordance with the purpose(s) of this invention, as embodied and broadly described herein, this invention, in one aspect, relates to methods of detecting the presence of a cancer by detecting a nucleic acid variation, truncation, or gene fusion within a nucleic acid of interest comprising conducting reverse transcription polymerase chain reaction (RT-PCR) on mRNA extracted from a tissue sample from a subject with a cancer; wherein the presence of amplification product or an increase in amplification product indicates the presence of a fusion, nucleotide variation, truncation, or excessive expression, thereby detecting the presence of a cancer. In particular, the invention, in one aspect, relates to methods of detecting the presence of a cancer by detecting the presence of one or more ALK related fusions, and/or the upregulated expression of wildtype ALK as may occur in certain cancers.

Additional advantages of the disclosed methods and compositions will be set forth in part in the description which follows, and in part will be understood from the description, or may be learned by practice of the disclosed method and compositions. The advantages of the disclosed methods and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1 shows representative ALK fusion proteins, chromosomal rearrangements that generate them, their occurrence in ALK-positive lymphomas and inflammatory myofibroblastic tumor (IMT) sarcomas, and their subcellular localizations. A partial listing of the more common oncogenic ALK fusions is shown (not shown: ALO17-ALK, CARS-ALK, MYH9-ALK, SEC31L1-ALK, MSN-ALK, and TFG$_{XL}$-ALK). C: cytosolic; N: nuclear; CM: cell membrane; NM: nuclear membrane. TPM3: tropomyosin-3; ATIC: 5-aminoimidazole-4-carboxamide ribonucleotide formyltransferase/IMP cyclohydrolase; CLTC: clathrin heavy chain; TFG: TRK-fused gene; TPM4: tropomyosin-4; MSN: moesin; RanBP2: Ran-binding protein 2; EML4: echinoderm mircrotubule-associated protein-like 4.

FIG. 3 shows additional forward and reverse primers for RT-PCR reactions to detect ALK fusions.

DETAILED DESCRIPTION

Figure 2:
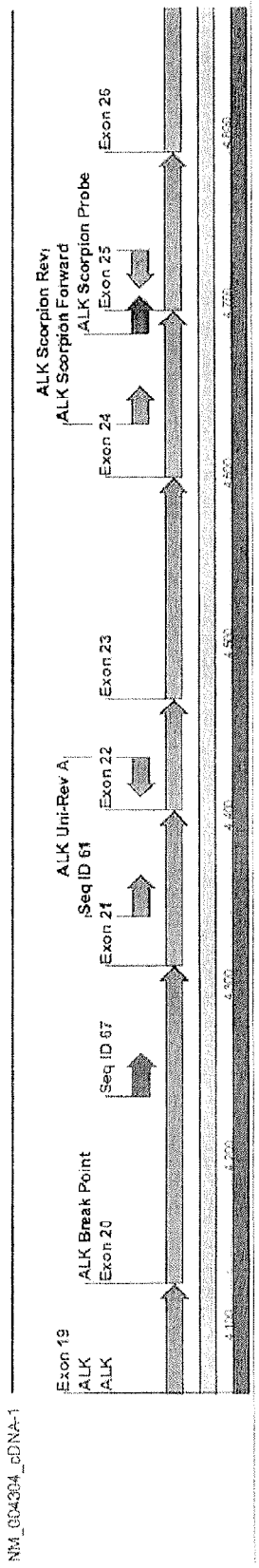
FIG. 2 shows

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value.

When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

An "increase" can refer to any change that results in a larger amount of a composition or compound, such as an amplification product relative to a control. Thus, for example, an increase in the amount in amplification products can include but is not limited to a 10%, 20%, 30%, 40%, 50%, 60%, 70%, 80%, 90%, or 100% increase. It is further contemplated herein that the detection an increase in expression or abundance of a DNA, mRNA, or protein relative to a control necessarily includes detection of the presence of the DNA, mRNA, or protein in situations where the DNA, mRNA, or protein is not present in the control.

"Obtaining a tissue sample" or "obtain a tissue sample" means to collect a sample of tissue from a subject or measure a tissue in a subject. It is understood and herein contemplated that tissue samples can be obtained by any means known in the art including invasive and non-invasive techniques. It is also understood that methods of measurement can be direct or indirect. Examples of methods of obtaining or measuring a tissue sample can include but are not limited to tissue biopsy, tissue lavage, aspiration, tissue swab, spinal tap, venipuncture, magnetic resonance imaging (MRI), Computed Tomography (CT) scan, Positron Emission Tomography (PET) scan, and X-ray (with and without contrast media).

The sensitive detection of a mutation at a known site in DNA is readily done with existing technologies. Allele specific primers can be designed to target a mutation at a known location such that its signal can be preferentially amplified over wildtype DNA. Unfortunately, this is not possible with unknown mutations that may occur at any position (base) in the target sequence.

Methods of Detecting an ALK-Related Cancer

The disclosed methods in one aspect related to methods of detection or diagnosis of the presence of a disease or condition such as a cancer, assessing the susceptibility or risk for a disease or condition such as a cancer, the monitoring of the progression of a disease or condition such as a cancer, and the determination of susceptibility or resistance to therapeutic treatment for a disease or condition such as a cancer in a subject comprising detecting the presence of nucleic acid or measuring the expression level of mRNA from a tissue sample from the subject; wherein the presence or an increase in the amount of amplification product indicates the presence of a cancer, and wherein the cancer is associated with a nucleic acid variation, truncation, overexpression, or gene fusion of ALK.

Anaplastic Lymphoma Kinase (ALK)

The ALK gene encodes a receptor tyrosine kinase (RTK) called ALK (SEQ ID NO: 1) (Genbank Accession No. U62540 (human coding sequence)) and is normally expressed primarily in the central and peripheral nervous systems. The 1620aa ALK polypeptide comprises a 1030aa extracellular domain which includes a 26aa amino-terminal signal peptide sequence, and binding sites located between residues 391 and 401. Additionally the ALK polypeptide comprises a kinase domain spanning Exons 21, 22, 23, 24, 25, and 26 (residues 1116-1383) which includes three tyrosines responsible for autophosphorylation within the activation loop at residues 1278, 1282, and 1283. ALK mutations have been shown to constitutively activate the kinase catalytic function of the ALK protein, with the deregulated mutant ALK in turn activating downstream cellular signaling proteins in pathways that promote aberrant cell proliferation. In fact, the mutations that result in dysregulated ALK kinase activity are associated with several types of cancers.

ALK fusions represent the most common mutation of this tyrosine kinase. Such fusions include but are not limited to nucleophosmin-ALK (NPM-ALK), 5-aminoimidazole-4-carboxamide ribonucleotide formyltransferase/IMP cyclohydrolase (ATIC-ALK), clathrin heavy chain-ALK (CLTC-ALK), kinesin-1 heavy chain gene-ALK (KIF5B-ALK); Ran-binding protein 2-ALK (RANBP2-ALK), SEC31L1-ALK, tropomyosin-3-ALK (TPM3-ALK), tropomyosin-4-ALK (TPM4-ALK), TRK-fused gene(Large)-ALK (TFG$_L$-ALK), TRK-fused gene(Small)-ALK (TFG$_S$-ALK), CARS-ALK, EML4-ALK, 5-aminoimidazole-4-carboxamide ribonucleotide formyltransferase/IMP cyclohydrolase-ALK (ATIC-ALK), ALO17-ALK, moesin-ALK (MSN-ALK), non-muscle myosin heavy chain gene-ALK (MYH9-ALK), and TRK-fused gene(Extra Large)-ALK (TFG$_{XL}$-ALK). Six ALK fusions, CARS-ALK. CLTC-ALK, RANBP2-ALK, SEC31L1-ALK, TPM3-ALK, and TPM4-ALK have been identified in IMTs. TPM3-ALK, TPM4-ALK and CLTC-ALK fusions have been detected in both classical T- or null-cell lymphomas and IMT sarcomas, whereas CARS-ALK, RANBP2-ALK, and SEC31L1-ALK occur in IMT. CLTC-ALK and NPM-ALK also occur in B-cell plasmablastic/immunoblastic lymphomas. The TPM4-ALK fusion occurs in esophageal squamous cell carcinomas, and the ALK fusion EML4-ALK, TFG-ALK and KIF5B-ALK are found in non-small cell lung cancers. EML4-ALK has also recently been identified in both colorectal and breast carcinomas as well. Therefore, in one aspect, disclosed herein are methods of detecting the presence of a cancer comprising an ALK fusion or ALK dysregulation (such as, for example, overexpression) comprising detecting the presence of or measuring the amount of nucleic acid associated with an ALK fusion from a tissue sample from a subject, wherein the an increase in a nucleic acid relative to a control or presence of a nucleic acid indicates the presence of an ALK fusion or ALK dysregulation (e.g., overexpression).

ALK fusions and ALK dysregulation (e.g., overexpression) are associated with several known cancer types. It is understood that one or more ALK fusions can be associated with a particular cancer. It is further understood that there are several types of cancer associated with ALK fusions and ALK overexpression including but not limited to anaplastic large-cell lymphoma (ALCL), neuroblastoma, breast cancer, ovarian cancer, colorectal carcinoma, non-small cell lung carcinoma, diffuse large B-cell lymphoma, esophageal squamous cell carcinoma, anaplastic large-cell lymphoma, neuroblastoma, inflammatory myofibroblastic tumors, malignant histiocytosis, and glioblastomas.

ALCL.

Anaplastic large-cell lymphomas comprise ~2.5% of all NHL; within the pediatric age group specifically, ~13% of all NHL (30-40% of all childhood large-cell lymphomas) are of this type. Studies of ALCL patients now divide this NHL into ALK-positive and ALK-negative subsets; ~60% of all ALCLs are caused by ALK fusions. For unclear reasons, ALK-positive ALCL patients fare significantly better following CHOP based multi-agent conventional chemotherapy than those with ALK-negative disease (with overall 5-year survivals of ~75% vs. ~35%, respectively). However, more than a third of patients suffer multiple relapses following chemotherapy, thus the 5-year disease-free survival of ALK-positive ALCL is only ~40%.

ALK+ Diffuse Large B-Cell Lymphoma.

In 2003, ALK fusions were shown to occur in a non-ALCL form of NHL with the description of CLTC-ALK or NPM-ALK in diffuse large B-cell lymphomas (ALK+DLB-CLs). Consistent with their B-lineage, these NHLs express cytoplasmic IgA and plasma cell markers, and possess an immunoblastic morphology. Translational research studies revealed the t(2;17) and CLTC-ALK mRNA in the majority of these lymphomas, while immunolabeling confirmed granular ALK staining identical to that observed in CLTC-ALK-positive ALCL. As for all other ALK fusion partner proteins, a self-association motif in the CLTC portion of CLTC-ALK mediates constitutive self-association and activation of the fusion kinase to drive lymphomagenesis. ALK+DLBCLs occur predominately in adults; however, the t(2;5) and NPM-ALK mRNA in pediatric lymphomas are phenotypically identical to CLTC-ALK-positive adult B-NHLs. Approximately 0.5-1% of all DLBCL is thought to be ALK-positive. The identification of DLBCLs caused by mutant ALK is important because patients with these lymphomas have outcomes that are much inferior to ALK-negative DLBCL patients following CHOP-based treatments; thus, ALK+DLBCL patients should strongly be considered as candidates for ALK-targeted kinase inhibitor therapy.

ALK+ Systemic Histiocytosis.

ALK fusions were described in 2008 in another hematopoietic neoplasm, systemic histiocytosis. Three cases of this previously uncharacterized form of histiocytosis, which presents in early infancy, exhibited ALK immunoreactivity and the one case analyzed molecularly expressed TPM3-ALK.

In addition to the aforementioned hematological malignancies in which constitutively activated ALK fusions have been shown to be a causative mechanism in many cases, the genesis of subsets of various solid tumors in some instances, very common human tumors such as non-small cell lung cancer, colorectal and breast cancers has recently been demonstrated to be due to aberrantly activated ALK.

Inflammatory Myofibroblastic Tumor.

The first non-hematopoietic tumor discovered to express ALK fusions was the sarcoma known as inflammatory myofibroblastic tumor (IMT), a spindle cell proliferation in the soft tissue and viscera of children and young adults (mean age at diagnosis ~10 years). Many IMTs are indolent and can be cured by resection. However, locally recurrent, invasive, and metastatic IMTs are not uncommon and current chemo- and radio-therapies are completely ineffective. Disclosed herein is the involvement of chromosome 2p23 (the location of the ALK gene) in IMTs, as well as ALK gene rearrangement. ALK immunoreactivity in 7 of 11 IMTs has been shown and TPM3-ALK and TPM4-ALK were identified in several cases. Additionally, two additional ALK fusions in IMT, CLTC- and RanBP2-ALK were identified. ALK fusions have also been examined by immunostaining in 73 IMTs, finding 60% (44 of the 73 cases) to be ALK-positive. Thus, ALK deregulation is of pathogenic importance in a majority of IMTs.

Non-Small Cell Lung Carcinoma.

The role of ALK fusions in cancer expanded further with the description of the novel EML4-ALK chimeric protein in 5 of 75 (6.7%) Japanese non-small cell lung carcinoma patients. Shortly thereafter, the existence of ALK fusions in lung cancer was corroborated by a different group who found 6 of 137 (4.4%) Chinese lung cancer patients to express ALK fusions (EML4-ALK, 3 pts; TFG-ALK, 1 pt; X-ALK. Two common themes have emerged—1) ALK fusions occur predominately in patients with adenocarcinoma (although occasional ALK-positive NSCLCs of squamous or mixed histologies are observed), mostly in individuals with minimal/no smoking history, and 2) ALK abnormalities usually occur exclusive of other common genetic abnormalities (e.g., EGFR and KRAS mutations). The exact percentage of NSCLCs caused by ALK fusions is not yet clear but estimates based on reports in the biomedical literature suggest a range of ~5-10%.

Esophageal Squamous Cell Carcinoma.

In 45 Iranian patients, a proteomics approach identified proteins under or over-represented in esophageal squamous cell carcinomas (ESCCs); TPM4-ALK was among those proteins over-represented. A second proteomics-based ESCC study—in this case, in Chinese patients—identified TPM4-ALK in these tumors as well.

Colorectal Carcinoma, Breast Cancer.

Three human tumor types—colorectal, breast, and non-small cell lung cancers were surveyed for the presence of the EML4-ALK fusion (other ALK mutations were not assessed in this study). In addition to confirming the expression of EML4-ALK in NSCLC (in 12 of 106 specimens studied, 11.3%), a subsets of breast (5 of 209 cases, 2.4%) and colorectal (2 of 83 cases, 2.4%) carcinomas were EML4-ALK-positive. In addition to known EML4-ALK variants 1 (E13; A20) and 2 (E20; A20), a novel variant (E21; A20) was found in colorectal carcinoma.

ALK in Familial and Sporadic Neuroblastoma.

Neuroblastoma is the most common extracranial solid tumor of childhood, and is derived from the developing neural crest. A small subset (~1-2%) of neuroblastomas exhibit a familial predisposition with an autosomal dominant inheritance. Most neuroblastoma patients have aggressive disease associated with survival probabilities <40% despite intensive chemo- and radio-therapy, and the disease accounts for ~15% of all childhood cancer mortality. ALK had previously been found to be constitutively activated also due to high-level over-expression as a result of gene amplification in a small number of neuroblastoma cell lines, in fact, ALK amplification occurs in ~15% of neuroblastomas in addition to activating point mutations. These missense mutations in ALK have been confirmed as activating mutations that drive neuroblastoma growth; furthermore, incubation of neuroblastoma cell lines with ALK small-molecule inhibitors reveal those cells with ALK activation (but not cell lines with normal levels of expression of wild-type ALK) to exhibit robust cytotoxic responses.

Recent studies demonstrate that inhibition of these mutant forms of ALK with small molecule drug candidates abrogates this abnormal cell proliferation and promotes apoptosis in neuroblastoma and other ALK-driven tumor cell lines. These discoveries highlight the need for a specialized diagnostic test for ALK mutations—a test that would have multiple clinical applications. For example, such an assay could be used to screen children in families affected with hereditary neuroblastoma to help facilitate the detection of tumors at an earlier stage when they are more amenable to treatment. Early detection and diagnosis of ALK-mediated cancers dramatically increases survival rates within the patient population. Thus, in one aspect disclosed herein are methods of detection or diagnosis of the presence of a disease or condition such as cancer, for example a cancer comprising overexpression or a fusion of anaplastic lymphoma kinase (ALK) the method comprising detecting the presence of or measuring the level or DNA, cDNA, or the expression level of mRNA associated with a nucleic acid variation, overexpression, truncation, or ALK fusions from a tissue sample from the subject; wherein the presence of or an increase in the amount of amplification product indicates the presence of an ALK related cancer (i.e., a cancer comprising overexpression of ALK, nucleic acid variation of ALK, truncation of ALK, or an ALK fusion). Also disclosed are methods of assessing the susceptibility or risk for a disease or condition, monitoring disease progression, or determination of susceptibility or resistance to therapeutic treatment for a cancer associated with a nucleic acid variation, truncation, or ALK fusion in a subject comprising detecting the presence of or measuring the level of DNA, cDNA, or the expression level of mRNA from a tissue sample from the subject; wherein the presence of an increase in the amount of amplification product relative to a control indicates the presence of an ALK related cancer.

It is understood and herein contemplated that in many tissues ALK is not present I normal tissue so detection of ALK indicates that ALK is being aberrantly overexpressed or expressed as a part of a fusion construct. Accordingly, detection of any portion of ALK can be sufficient for the diagnosis of a cancer comprising an ALK fusion or ALK dysregulation (such as, for example, overexpression). For example, detection of ALK kinase in a tissue sample can indicate the presence of a cancer comprising an ALK fusion or ALK overexpression. Therefore, disclosed herein are methods of diagnosing an anaplastic lymphoma kinase (ALK) related cancer in a subject comprising detecting the presence or measuring the expression level of mRNA from a tissue sample from the subject; wherein the mRNA is specific to ALK; and wherein an increase in the amount of mRNA relative to a control or the presence of ALK mRNA indicates the presence of an ALK related cancer. Also disclosed herein are methods of diagnosing a cancer comprising an ALK fusion in a human subject the method comprising conducting a nucleic acid amplification process on a tissue sample from the subject and detecting the presence of nucleic acid associated with the ALK kinase domain in the tissue sample. Accordingly, in one aspect, disclosed herein are methods of diagnosing a cancer comprising an ALK fusion in a human subject the method comprising conducting a nucleic acid amplification process on a tissue sample from the subject and detecting the presence of nucleic acid associated with the ALK kinase domain in the tissue sample. Also disclosed are methods of detecting the presence a cancer comprising an ALK fusion or overexpression of ALK in a tissue sample from a human subject with a cancer comprising performing a Polymerase Chain Reaction (PCR) reaction on the nucleic acid from the tissue sample, wherein the PCR reaction comprises at least one forward primer and at least one reverse primer that specifically hybridizes to a nucleic acid encoding the kinase of ALK as set forth in SEQ ID NO: 1, and detecting the presence or absence of the kinase domain of ALK, wherein the presence of the kinase domain of ALK indicates the presence of an ALK fusion.

It is further understood that the disclosed methods can be used to diagnose or detect the presence of any cancer comprising an ALK fusion, variation or truncation of ALK, or dysregulation of ALK (an aberrant expression such as overexpression) wherein the cancer is selected from the group consisting of neuroblastoma, breast cancer, ovarian cancer, colorectal carcinoma, non-small cell lung carcinoma, diffuse large B-cell lymphoma, esophageal squamous cell carcinoma, anaplastic large-cell lymphoma, neuroblastoma, inflammatory myofibroblastic tumors, malignant histiocytosis, and glioblastomas.

ALK fusion related cancers can be treated with ALK kinase inhibitors. However, ALK kinase inhibitor resistant cancers have also been discovered. These cancers are ALK fusions that further comprise point mutations of ALK in familial and sporadic cancers (e.g., neuroblastoma, breast cancer, ovarian cancer, colorectal carcinoma, non-small cell lung carcinoma, diffuse large B-cell lymphoma, esophageal squamous cell carcinoma, anaplastic large-cell lymphoma, neuroblastoma, inflammatory myofibroblastic tumors, malignant histiocytosis, and glioblastomas). The mutations in ALK result in constitutive activation of ALK. Accordingly ALK associated cancers are driven by these activating point mutations. Mutations in the tyrosine kinase catalytic domain M1166R, A1168P, I1171N, F1174I, F1174L, R1192P, F1245C, F1245V, F1245L, F1245I, I1250T, and R1275Q and in the extracellular domain at V476A are associated with neuroblastoma. Mutations at R401Q, A1168P, and V757M were identified in colorectal carcinomas. Additionally, mutations at L560F were identified in breast cancer, and at A877S in ovarian cancer. Thus, in one aspect, detecting the presence of a cancer is accomplished through the detection of point mutations in the sequence of ALK (i.e., by detecting the point mutation, an ALK-related cancer is identified). Thus, disclosed herein are methods of detecting the presence of an ALK related cancer, wherein the cancer further comprises one or more point mutations in ALK or wildtype ALK upregulation.

The disclosed ALK fusions can also cause deregulation of wildtype ALK. The dysregulated wildtype ALK can result an increase in wildtype ALK being produced as well as the disregulation of the kinase catalytic activity. Alternatively, a cancer can have a primary molecular pathology from another receptor tyrosine kinase (RTK) such as, cMET or IGFR, but develop resistance to inhibitors through parallel path activation of signaling pathways through ALK. Thus, another means for detecting the presence of a cancer is through the detection of an increase in wildtype ALK expression. Additionally, truncated wildtype ALK genes missing regulatory regions can result in constitutive ALK kinase catalytic function. Therefore, disclosed herein are methods of diagnosing the presence of a cancer comprising detecting the presence or relative increase in the expression of mRNA relating to a truncated ALK sequence.

It is understood and herein contemplated that the cause of an ALK related cancer can be due not only dysregulation of wildtype ALK or known ALK fusions, but one or more unidentified ALK fusions. Methods that are only able to detect known fusions would be unable to detect previously unknown fusions or mutations of ALK. By detecting not only the presence of a truncation, nucleic acid variation of ALK or an ALK fusion, but also detecting the presence of wildtype ALK and ALK kinase activity, the skilled artisan can determine if the cancer is due to dysregulated wildtype ALK, a known ALK fusion, or a previously unidentified ALK fusion or mutation of ALK. Accordingly, disclosed herein are methods for diagnosing a cancer, assessing the susceptibility or risk or a cancer, or detecting the presence of dysregulation of ALK comprising detecting the presence of an ALK kinase domain, wherein the presence of an ALK kinase domain indicates the presence of a cancer, susceptibility or risk or a cancer, or the presence of dysregulation of ALK. In some aspect, it may be advantageous to further distinguish whether the ALK presence was due to dysregulation of wild-type ALK or a fusion. Therefore, in one aspect, disclosed herein are methods further comprising detecting the presence of ALK extracellular region DNA, cDNA, RNA, or mRNA. Thus, for example, disclosed herein are methods of diagnosing or detecting the presence of a cancer comprising an ALK fusion or dysregulation of ALK comprising detecting the presence of nucleic acid associated with a kinase domain and the extracellular region of ALK as set forth in SEQ ID NO: 1 from a tissue sample in a subject, wherein presence of both the extracellular region and the kinase domain indicates dysregulation of a wild-type ALK and presence of an ALK kinase domain and absence of an ALK extracellular region indicates a fusion.

In one aspect, it is understood that the detection of the presence or absence of an ALK dysregulation such as an ALK fusion can dictate a particular treatment regimen. For example, once a determination detection of an ALK amplification product (such as, for example, an ALK kinase) is made and therefore an ALK dysregulation such as an ALK fusion, the method can further comprise treating the subject with an ALK kinase inhibitor. Where a determination is made that ALK amplification product (such as, for example, an ALK kinase) is not present, the method can further comprise administering a treatment regimen that does not include an ALK inhibitor. Thus, in one aspect, disclosed herein are methods of treating a cancer comprising an ALK fusion or dysregulation of ALK (e.g., ALk overexpression) comprising conducting a nucleic acid amplification process on a tissue sample from the subject and detecting the presence of nucleic acid associated with the ALK kinase domain in the tissue sample, wherein the presence of nucleic acid associated with the ALK kinase domain indicates a cancer comprising an ALK fusion or ALK overexpression; and administering an ALK inhibitor to the subject.

mRNA Detection and Quantification

The methods disclosed herein relate to the detection of nucleic acid variation in the form of, for example, point mutations and truncations, or the detection of expression of ALK fusions, aberrant wildtype ALK expression (e.g., overexpression), or expression of ALK truncation mutants. For these latter expression level detections, the methods comprise detecting either the abundance or presence of mRNA, or both. Thus, disclosed herein are methods and compositions for diagnosing or detecting the presence of a cancer comprising an ALK fusion, dysregulation of ALK (e.g., overexpression of ALK), or variation or truncation of ALK in a subject by the method comprising measuring the presence or level of mRNA from a tissue sample from the subject; wherein an increase in the amount of mRNA relative to a control or the presence of ALK mRNA indicates the presence of an ALK related cancer.

A number of widely used procedures exist for detecting and determining the abundance of a particular mRNA in a total or poly(A) RNA sample. For example, specific mRNAs can be detected using Northern blot analysis, nuclease protection assays (NPA), in situ hybridization, or reverse transcription-polymerase chain reaction (RT-PCR), real-time PCR, real-time RT-PCR, and microarray. Therefore, also disclosed herein are methods of diagnosing a cancer comprising an ALK fusion in a human subject the method comprising conducting a nucleic acid amplification process on a tissue sample from the subject and detecting the presence of nucleic acid associated with the ALK kinase domain in the tissue sample, wherein the nucleic acid amplification process is RT-PCR or real-time PCR. Also disclosed are methods of diagnosing a cancer wherein the RT-PCR or real-time PCR reaction comprises a forward and reverse primer pair that specifically hybridize to an ALK kinase domain sequence.

In another embodiment, disclosed herein are methods of detecting the presence a cancer comprising an ALK fusion or overexpression of ALK in a tissue sample from a human subject with a cancer comprising performing a Polymerase Chain Reaction (PCR) reaction on the nucleic acid from the tissue sample, wherein the PCR reaction comprises at least one forward primer and at least one reverse primer that specifically hybridizes to a nucleic acid encoding the kinase of ALK as set forth in SEQ ID NO: 1, and detecting the presence or absence of the kinase domain of ALK, wherein the presence of the kinase domain of ALK indicates the presence of an ALK fusion, and wherein the pCR reaction is a reverse transcription PCR (RT-PCR), real-time PCR, or real-time RT-PCR reaction.

In theory, each of these techniques can be used to detect specific RNAs and to precisely determine their expression level. In general, Northern analysis is the only method that provides information about transcript size, whereas NPAs are the easiest way to simultaneously examine multiple messages. In situ hybridization is used to localize expression of a particular gene within a tissue or cell type, and RT-PCR is the most sensitive method for detecting and quantitating gene expression.

RT-PCR allows for the detection of the RNA transcript of any gene, regardless of the scarcity of the starting material or relative abundance of the specific mRNA. In RT-PCR, an RNA template is copied into a complementary DNA (cDNA) using a retroviral reverse transcriptase. The cDNA is then amplified exponentially by PCR using a DNA polymerase. The reverse transcription and PCR reactions can occur in the same or difference tubes. RT-PCR is somewhat tolerant of degraded RNA. As long as the RNA is intact within the region spanned by the primers, the target will be amplified.

Relative quantitative RT-PCR involves amplifying an internal control simultaneously with the gene of interest. The internal control is used to normalize the samples. Once normalized, direct comparisons of relative abundance of a specific mRNA can be made across the samples. It is crucial to choose an internal control with a constant level of expression across all experimental samples (i.e., not affected by experimental treatment). Commonly used internal controls (e.g., GAPDH, β-actin, cyclophilin) often vary in expression and, therefore, may not be appropriate internal controls. Additionally, most common internal controls are expressed at much higher levels than the mRNA being studied. For relative RT-PCR results to be meaningful, all products of the PCR reaction must be analyzed in the linear range of amplification. This becomes difficult for transcripts of widely different levels of abundance.

Competitive RT-PCR is used for absolute quantitation. This technique involves designing, synthesizing, and accurately quantitating a competitor RNA that can be distinguished from the endogenous target by a small difference in size or sequence. Known amounts of the competitor RNA are added to experimental samples and RT-PCR is performed. Signals from the endogenous target are compared with signals from the competitor to determine the amount of target present in the sample.

Thus, disclosed herein in one aspect are methods of diagnosing an anaplastic lymphoma kinase (ALK) related cancer in a subject comprising conducting an RT-PCR reaction on mRNA from a tissue sample from the subject; wherein the reverse transcription polymerase chain reaction (RT-PCR) comprises a reverse primer capable of specifically hybridizing to one or more ALK kinase domain sequences and at least one forward primer capable of specifically hybridizing to one or more ALK kinase domain sequences; and wherein an increase in the amount of amplification product or the mere presence of amplification product indicates the presence of an ALK related cancer. As the disclosed methods can be used to detect wildtype ALK, ALK fusions, and ALK kinase domain activity, also disclosed herein are methods of diagnosing an anaplastic lymphoma kinase (ALK) related cancer or detecting the dysregulation of an ALK kinase in a subject comprising conducting a first RT-PCR reaction on mRNA from a tissue sample from the subject; wherein the reverse transcription polymerase chain reaction (RT-PCR) comprises a reverse primer capable of specifically hybridizing to one or more ALK kinase sequences and at least one forward primer wherein the forward primer specifically hybridizes to an ALK kinase sequence. The methods can further comprise a second RT-PCR reaction on mRNA from a tissue sample from the subject; wherein the reverse transcription polymerase chain reaction (RT-PCR) comprises a forward and reverse primer capable of specifically hybridizing to one or more ALK sequences (e.g., an ALK extracellular region); wherein the reverse transcription polymerase chain reaction (RT-PCR) comprises a forward and reverse primer capable of specifically hybridizing to one or more ALK kinase domain sequences; and wherein the presence of an amplicon the presence of or the increase in the amount of amplification product relative to a control indicates the presence of an ALK related cancer and the presence of dysregulation of ALK kinase.

Northern analysis is the easiest method for determining transcript size, and for identifying alternatively spliced transcripts and multigene family members. It can also be used to directly compare the relative abundance of a given message between all the samples on a blot. The Northern blotting procedure is straightforward and provides opportunities to evaluate progress at various points (e.g., intactness of the RNA sample and how efficiently it has transferred to the membrane). RNA samples are first separated by size via electrophoresis in an agarose gel under denaturing conditions. The RNA is then transferred to a membrane, cross-linked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

The Nuclease Protection Assay (NPA) (including both ribonuclease protection assays and S1 nuclease assays) is a sensitive method for the detection and quantitation of specific mRNAs. The basis of the NPA is solution hybridization of an antisense probe (radiolabeled or nonisotopic) to an RNA sample. After hybridization, single-stranded, unhybridized probe and RNA are degraded by nucleases. The remaining protected fragments are separated on an acrylamide gel. Solution hybridization is typically more efficient than membrane-based hybridization, and it can accommodate up to 100 µg of sample RNA, compared with the 20-30 µg maximum of blot hybridizations. NPAs are also less sensitive to RNA sample degradation than Northern analysis since cleavage is only detected in the region of overlap with the probe (probes are usually about 100-400 bases in length).

NPAs are the method of choice for the simultaneous detection of several RNA species. During solution hybridization and subsequent analysis, individual probe/target interactions are completely independent of one another. Thus, several RNA targets and appropriate controls can be assayed simultaneously (up to twelve have been used in the same reaction), provided that the individual probes are of different lengths. NPAs are also commonly used to precisely map mRNA termini and intron/exon junctions.

In situ hybridization (ISH) is a powerful and versatile tool for the localization of specific mRNAs in cells or tissues. Unlike Northern analysis and nuclease protection assays, ISH does not require the isolation or electrophoretic separation of RNA. Hybridization of the probe takes place within the cell or tissue. Since cellular structure is maintained throughout the procedure, ISH provides information about the location of mRNA within the tissue sample.

The procedure begins by fixing samples in neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents.

DNA Detection and Quantification

The methods disclosed herein relate to the detection of nucleic acid variation in the form of, for example, point mutations and truncations, or the detection of expression of ALK fusions, aberrant wildtype ALK expression, or expression of ALK truncation mutants. For these latter expression level detections, the methods comprise detecting either the abundance or presence of mRNA, or both. Alternatively, detection can directed to the abundance or presence of DNA, for example, cDNA. Thus, disclosed herein are methods and compositions for diagnosing an anaplastic lymphoma kinase (ALK) related cancer (such as, for example a cancer comprising an ALK fusion) in a subject comprising measuring the presence or level of DNA from a tissue sample from the subject; wherein the presence or an increase in the amount of DNA indicates the presence of an ALK related cancer. It is understood and herein contemplated that the primers used in the pCR reaction can be a forward and reverse primer pair that can specifically hybridize to an ALK kinase domain (such as, for example, on or more of exons 21, 22, 23, 24, 25, or 26 of ALK). It is also understood that the disclosed methods can be performed and measured relative to a negative control.

A number of widely used procedures exist for detecting and determining the abundance of a particular DNA in a sample. For example, the technology of PCR permits amplification and subsequent detection of minute quantities of a target nucleic acid. Details of PCR are well described in the art, including, for example, U.S. Pat. No. 4,683,195 to Mullis et al., U.S. Pat. No. 4,683,202 to Mullis and U.S. Pat. No. 4,965,188 to Mullis et al. Generally, oligonucleotide primers are annealed to the denatured strands of a target nucleic acid, and primer extension products are formed by the polymerization of deoxynucleoside triphosphates by a polymerase. A typical PCR method involves repetitive cycles of template nucleic acid denaturation, primer annealing and extension of the annealed primers by the action of a thermostable polymerase. The process results in exponential amplification of the target nucleic acid, and thus allows the detection of targets existing in very low concentrations in a sample. It is understood and herein contemplated that there are variant PCR methods known in the art that may also be utilized in the disclosed methods, for example, Quantitative PCR (QPCR); microarrays, real-time PCT; hot start PCR; nested PCR; allele-specific PCR; and Touchdown PCR.

Microarrays

An array is an orderly arrangement of samples, providing a medium for matching known and unknown DNA samples based on base-pairing rules and automating the process of identifying the unknowns. An array experiment can make use of common assay systems such as microplates or standard blotting membranes, and can be created by hand or make use of robotics to deposit the sample. In general, arrays are described as macroarrays or microarrays, the difference being the size of the sample spots. Macroarrays contain sample spot sizes of about 300 microns or larger and can be easily imaged by existing gel and blot scanners. The sample spot sizes in microarray can be 300 microns or less, but typically less than 200 microns in diameter and these arrays usually contains thousands of spots. Microarrays require specialized robotics and/or imaging equipment that generally are not commercially available as a complete system. Terminologies that have been used in the literature to describe this technology include, but not limited to: biochip, DNA chip, DNA microarray, GeneChip® (Affymetrix, Inc which refers to its high density, oligonucleotide-based DNA arrays), and gene array.

DNA microarrays, or DNA chips are fabricated by high-speed robotics, generally on glass or nylon substrates, for which probes with known identity are used to determine complementary binding, thus allowing massively parallel gene expression and gene discovery studies. An experiment with a single DNA chip can provide information on thousands of genes simultaneously. It is herein contemplated that the disclosed microarrays can be used to monitor gene expression, disease diagnosis, gene discovery, drug discovery (pharmacogenomics), and toxicological research or toxicogenomics.

There are two variants of the DNA microarray technology, in terms of the property of arrayed DNA sequence with known identity. Type I microarrays comprise a probe cDNA (500~5,000 bases long) that is immobilized to a solid surface such as glass using robot spotting and exposed to a set of targets either separately or in a mixture. This method is traditionally referred to as DNA microarray. With Type I microarrays, localized multiple copies of one or more polynucleotide sequences, preferably copies of a single polynucleotide sequence are immobilized on a plurality of defined regions of the substrate's surface. A polynucleotide refers to a chain of nucleotides ranging from 5 to 10,000 nucleotides. These immobilized copies of a polynucleotide sequence are suitable for use as probes in hybridization experiments.

To prepare beads coated with immobilized probes, beads are immersed in a solution containing the desired probe sequence and then immobilized on the beads by covalent or noncovalent means. Alternatively, when the probes are immobilized on rods, a given probe can be spotted at defined regions of the rod. Typical dispensers include a micropipette delivering solution to the substrate with a robotic system to control the position of the micropipette with respect to the substrate. There can be a multiplicity of dispensers so that reagents can be delivered to the reaction regions simultaneously. In one embodiment, a microarray is formed by using ink-jet technology based on the piezoelectric effect, whereby a narrow tube containing a liquid of interest, such as oligonucleotide synthesis reagents, is encircled by an adapter. An electric charge sent across the adapter causes the adapter to expand at a different rate than the tube and forces a small drop of liquid onto a substrate.

Tissue samples may be any sample containing polynucleotides (polynucleotide targets) of interest and obtained from any bodily fluid (blood, urine, saliva, phlegm, gastric juices, etc.), cultured cells, biopsies, or other tissue preparations. DNA or RNA can be isolated from the sample according to any of a number of methods well known to those of skill in the art. In one embodiment, total RNA is isolated using the TRIzol total RNA isolation reagent (Life Technologies, Inc., Rockville, Md.) and RNA is isolated using oligo d(T) column chromatography or glass beads. After hybridization and processing, the hybridization signals obtained should reflect accurately the amounts of control target polynucleotide added to the sample.

The plurality of defined regions on the substrate can be arranged in a variety of formats. For example, the regions may be arranged perpendicular or in parallel to the length of the casing. Furthermore, the targets do not have to be directly bound to the substrate, but rather can be bound to the substrate through a linker group. The linker groups may typically vary from about 6 to 50 atoms long. Linker groups include ethylene glycol oligomers, diamines, diacids and the like. Reactive groups on the substrate surface react with one of the terminal portions of the linker to bind the linker to the substrate. The other terminal portion of the linker is then functionalized for binding the probes.

Sample polynucleotides may be labeled with one or more labeling moieties to allow for detection of hybridized probe/target polynucleotide complexes. The labeling moieties can include compositions that can be detected by spectroscopic, photochemical, biochemical, bioelectronic, immunochemical, electrical, optical or chemical means. The labeling moieties include radioisotopes, such as $^{32}P$, $^{33}P$ or $^{35}S$, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, biotin, and the like.

Labeling can be carried out during an amplification reaction, such as polymerase chain reaction and in vitro or in vivo transcription reactions. Alternatively, the labeling moiety can be incorporated after hybridization once a probe-target complex his formed. In one embodiment, biotin is first incorporated during an amplification step as described above. After the hybridization reaction, unbound nucleic acids are rinsed away so that the only biotin remaining bound to the substrate is that attached to target polynucleotides that are hybridized to the polynucleotide probes. Then, an avidin-conjugated fluorophore, such as avidin-phycoerythrin, that binds with high affinity to biotin is added.

Hybridization causes a polynucleotide probe and a complementary target to form a stable duplex through base pairing. Hybridization methods are well known to those skilled in the art Stringent conditions for hybridization can be defined by salt concentration, temperature, and other chemicals and conditions. Varying additional parameters, such as hybridization time, the concentration of detergent (sodium dodecyl sulfate, SDS) or solvent (formamide), and the inclusion or exclusion of carrier DNA, are well known to those skilled in the art. Additional variations on these conditions will be readily apparent to those skilled in the art.

Methods for detecting complex formation are well known to those skilled in the art. In one embodiment, the polynucleotide probes are labeled with a fluorescent label and measurement of levels and patterns of complex formation is accomplished by fluorescence microscopy, preferably confocal fluorescence microscopy. An argon ion laser excites the fluorescent label, emissions are directed to a photomultiplier and the amount of emitted light detected and quantitated. The detected signal should be proportional to the amount of probe/target polynucleotide complex at each position of the microarray. The fluorescence microscope can be associated with a computer-driven scanner device to generate a quantitative two-dimensional image of hybridization intensities. The scanned image is examined to determine the abundance/expression level of each hybridized target polynucleotide.

In a differential hybridization experiment, polynucleotide targets from two or more different biological samples are labeled with two or more different fluorescent labels with different emission wavelengths. Fluorescent signals are detected separately with different photomultipliers set to detect specific wavelengths. The relative abundances/expression levels of the target polynucleotides in two or more samples is obtained. Typically, microarray fluorescence intensities can be normalized to take into account variations in hybridization intensities when more than one microarray is used under similar test conditions. In one embodiment, individual polynucleotide probe/target complex hybridization intensities are normalized using the intensities derived from internal normalization controls contained on each microarray.

Type II microarrays comprise an array of oligonucleotides (20~80-mer oligos) or peptide nucleic acid (PNA) probes that is synthesized either in situ (on-chip) or by conventional synthesis followed by on-chip immobilization. The array is exposed to labeled sample DNA, hybridized, and the identity/abundance of complementary sequences are determined. This method, "historically" called DNA chips, was developed at Affymetrix, Inc., which sells its photolithographically fabricated products under the GeneChip® trademark.

The basic concept behind the use of Type II arrays for gene expression is simple: labeled cDNA or cRNA targets derived from the mRNA of an experimental sample are hybridized to nucleic acid probes attached to the solid support. By monitoring the amount of label associated with each DNA location, it is possible to infer the abundance of each mRNA species represented. Although hybridization has been used for decades to detect and quantify nucleic acids, the combination of the miniaturization of the technology and the large and growing amounts of sequence information, have enormously expanded the scale at which gene expression can be studied.

Microarray manufacturing can begin with a 5-inch square quartz wafer. Initially the quartz is washed to ensure uniform hydroxylation across its surface. Because quartz is naturally hydroxylated, it provides an excellent substrate for the attachment of chemicals, such as linker molecules, that are later used to position the probes on the arrays.

The wafer is placed in a bath of silane, which reacts with the hydroxyl groups of the quartz, and forms a matrix of covalently linked molecules. The distance between these silane molecules determines the probes' packing density, allowing arrays to hold over 500,000 probe locations, or features, within a mere 1.28 square centimeters. Each of these features harbors millions of identical DNA molecules. The silane film provides a uniform hydroxyl density to initiate probe assembly. Linker molecules, attached to the silane matrix, provide a surface that may be spatially activated by light.

Probe synthesis occurs in parallel, resulting in the addition of an A, C, T, or G nucleotide to multiple growing chains simultaneously. To define which oligonucleotide chains will receive a nucleotide in each step, photolithographic masks, carrying 18 to 20 square micron windows that correspond to the dimensions of individual features, are placed over the coated wafer. The windows are distributed over the mask based on the desired sequence of each probe. When ultraviolet light is shone over the mask in the first step of synthesis, the exposed linkers become deprotected and are available for nucleotide coupling.

Once the desired features have been activated, a solution containing a single type of deoxynucleotide with a removable protection group is flushed over the wafer's surface. The nucleotide attaches to the activated linkers, initiating the synthesis process.

Although each position in the sequence of an oligonucleotide can be occupied by 1 of 4 nucleotides, resulting in an apparent need for 25×4, or 100, different masks per wafer, the synthesis process can be designed to significantly reduce this requirement. Algorithms that help minimize mask usage calculate how to best coordinate probe growth by adjusting synthesis rates of individual probes and identifying situations when the same mask can be used multiple times.

Some of the key elements of selection and design are common to the production of all microarrays, regardless of their intended application. Strategies to optimize probe hybridization, for example, are invariably included in the process of probe selection. Hybridization under particular pH, salt, and temperature conditions can be optimized by taking into account melting temperatures and using empirical rules that correlate with desired hybridization behaviors.

To obtain a complete picture of a gene's activity, some probes are selected from regions shared by multiple splice or polyadenylation variants. In other cases, unique probes that distinguish between variants are favored. Inter-probe distance is also factored into the selection process.

A different set of strategies is used to select probes for genotyping arrays that rely on multiple probes to interrogate individual nucleotides in a sequence. The identity of a target base can be deduced using four identical probes that vary only in the target position, each containing one of the four possible bases.

Alternatively, the presence of a consensus sequence can be tested using one or two probes representing specific alleles. To genotype heterozygous or genetically mixed samples, arrays with many probes can be created to provide redundant information, resulting in unequivocal genotyping. In addition, generic probes can be used in some applications to maximize flexibility. Some probe arrays, for example, allow the separation and analysis of individual reaction products from complex mixtures, such as those used in some protocols to identify single nucleotide polymorphisms (SNPs).

In one aspect, disclosed herein are microarrays wherein an oligonucleotide probe in use on the microarray specifically hybridizes to an ALK kinase domain (for example, hybridization occurs along exons 21, 22, 23, 24, 25, 26 of ALK or a combination thereof). In one aspect, disclosed herein are methods of diagnosing a cancer comprising an ALK fusion or aberrant ALK expression (i.e., dysregulation) comprising applying a tissue sample to a microarray and detecting the presence or an increase in ALK kinase, wherein the microarray comprises an oligonucleotide probe or primers that specifically hybridize to one or more portions of the ALK kinase domain as set forth in SEQ ID NO: 1.

Real-Time PCR

Real-time PCR monitors the fluorescence emitted during the reaction as an indicator of amplicon production during each PCR cycle (i.e., in real time) as opposed to the endpoint detection. The real-time progress of the reaction can be viewed in some systems. Real-time PCR does not detect the size of the amplicon and thus does not allow the differentiation between DNA and cDNA amplification, however, it is not influenced by non-specific amplification unless SYBR Green is used. Real-time PCR quantitation eliminates post-PCR processing of PCR products. This helps to increase throughput and reduce the chances of carryover contamination. Real-time PCR also offers a wide dynamic range of up to $10^7$-fold. Dynamic range of any assay determines how much target concentration can vary and still be quantified. A wide dynamic range means that a wide range of ratios of target and normaliser can be assayed with equal sensitivity and specificity. It follows that the broader the dynamic range, the more accurate the quantitation. When combined with RT-PCR, a real-time RT-PCR reaction reduces the time needed for measuring the amount of amplicon by providing for the visualization of the amplicon as the amplification process is progressing.

The real-time PCR system is based on the detection and quantitation of a fluorescent reporter. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed. A significant increase in fluorescence above the baseline value measured during the 3-15 cycles can indicate the detection of accumulated PCR product.

A fixed fluorescence threshold is set significantly above the baseline that can be altered by the operator. The parameter $C_T$ (threshold cycle) is defined as the cycle number at which the fluorescence emission exceeds the fixed threshold.

There are three main fluorescence-monitoring systems for DNA amplification: (1) hydrolysis probes; (2) hybridising probes; and (3) DNA-binding agents. Hydrolysis probes include TaqMan probes, molecular beacons and scorpions. They use the fluorogenic 5' exonuclease activity of Taq polymerase to measure the amount of target sequences in cDNA samples.

TaqMan probes are oligonucleotides longer than the primers (20-30 bases long with a Tm value of 10° C. higher) that contain a fluorescent dye usually on the 5' base, and a quenching dye (usually TAMRA) typically on the 3' base. When irradiated, the excited fluorescent dye transfers energy to the nearby quenching dye molecule rather than fluorescing (this is called FRET=Förster or fluorescence resonance energy transfer). Thus, the close proximity of the reporter and quencher prevents emission of any fluorescence while the probe is intact. TaqMan probes are designed to anneal to an internal region of a PCR product. When the polymerase replicates a template on which a TaqMan probe is bound, its 5' exonuclease activity cleaves the probe. This ends the activity of quencher (no FRET) and the reporter dye starts to emit fluorescence which increases in each cycle proportional to the rate of probe cleavage. Accumulation of PCR products is detected by monitoring the increase in fluorescence of the reporter dye (note that primers are not labelled). TaqMan assay uses universal thermal cycling parameters and PCR reaction conditions. Because the cleavage occurs only if the probe hybridises to the target, the origin of the detected fluorescence is specific amplification. The process of hybridisation and cleavage does not interfere with the exponential accumulation of the product. One specific requirement for fluorogenic probes is that there be no G at the 5' end. A 'G' adjacent to the reporter dye can quench reporter fluorescence even after cleavage.

Molecular beacons also contain fluorescent (FAM, TAMRA, TET, ROX) and quenching dyes (typically DABCYL) at either end but they are designed to adopt a hairpin structure while free in solution to bring the fluorescent dye and the quencher in close proximity for FRET to occur. They have two arms with complementary sequences that form a very stable hybrid or stem. The close proximity of the reporter and the quencher in this hairpin configuration suppresses reporter fluorescence. When the beacon hybridises to the target during the annealing step, the reporter dye is separated from the quencher and the reporter fluoresces (FRET does not occur). Molecular beacons remain intact during PCR and must rebind to target every cycle for fluorescence emission. This will correlate to the amount of PCR product available. All real-time PCR chemistries allow detection of multiple DNA species (multiplexing) by designing each probe/beacon with a spectrally unique fluor/quench pair as long as the platform is suitable for melting curve analysis if SYBR green is used. By multiplexing, the target(s) and endogenous control can be amplified in single tube.

With Scorpion probes, sequence-specific priming and PCR product detection is achieved using a single oligonucleotide. The Scorpion probe maintains a stem-loop configuration in the unhybridised state. The fluorophore is attached to the 5' end and is quenched by a moiety coupled to the 3' end. The 3' portion of the stem also contains sequence that is complementary to the extension product of the primer. This sequence is linked to the 5' end of a specific primer via a non-amplifiable monomer. After extension of the Scorpion primer, the specific probe sequence is able to bind to its complement within the extended amplicon thus opening up the hairpin loop. This prevents the fluorescence from being quenched and a signal is observed. In one aspect the forward and/or reverse primer of the disclosed kits and methods of diagnosis or detection can be a scorpion primer. For example, the reverse primer can be a reverse primer that specifically hybridizes the ALK kinase domain and further comprises a scorpion probe, such as, for example, SEQ ID NO: 2.

Another alternative is the double-stranded DNA binding dye chemistry, which quantitates the amplicon production (including non-specific amplification and primer-dimer complex) by the use of a non-sequence specific fluorescent intercalating agent (SYBR-green I or ethidium bromide). It does not bind to ssDNA. SYBR green is a fluorogenic minor groove binding dye that exhibits little fluorescence when in solution but emits a strong fluorescent signal upon binding to double-stranded DNA. Disadvantages of SYBR green-based real-time PCR include the requirement for extensive optimisation. Furthermore, non-specific amplifications require follow-up assays (melting point curve or dissociation analysis) for amplicon identification. The method has been used in HFE-C282Y genotyping. Another controllable problem is that longer amplicons create a stronger signal (if combined with other factors, this may cause CDC camera saturation, see below). Normally SYBR green is used in singleplex reactions, however when coupled with melting point analysis, it can be used for multiplex reactions.

The threshold cycle or the $C_T$ value is the cycle at which a significant increase in ΔRn is first detected (for definition of ΔRn, see below). The threshold cycle is when the system begins to detect the increase in the signal associated with an exponential growth of PCR product during the log-linear phase. This phase provides the most useful information about the reaction (certainly more important than the end-point). The slope of the log-linear phase is a reflection of the amplification efficiency. The efficiency (Eff) of the reaction can be calculated by the formula: $Eff=10^{(-1/slope)}-1$. The efficiency of the PCR should be 90-100% (3.6>slope>3.1). A number of variables can affect the efficiency of the PCR. These factors include length of the amplicon, secondary structure and primer quality. Although valid data can be obtained that fall outside of the efficiency range, the qRT-PCR should be further optimised or alternative amplicons designed. For the slope to be an indicator of real amplification (rather than signal drift), there has to be an inflection point. This is the point on the growth curve when the log-linear phase begins. It also represents the greatest rate of change along the growth curve. (Signal drift is characterised by gradual increase or decrease in fluorescence without amplification of the product.) The important parameter for quantitation is the $C_T$. The higher the initial amount of genomic DNA, the sooner accumulated product is detected in the PCR process, and the lower the $C_T$ value. The threshold should be placed above any baseline activity and within the exponential increase phase (which looks linear in the log transformation). Some software allows determination of the cycle threshold ($C_T$) by a mathematical analysis of the growth curve. This provides better run-to-run reproducibility. A $C_T$ value of 40 means no amplification and this value cannot be included in the calculations. Besides being used for quantitation, the $C_T$ value can be used for qualitative analysis as a pass/fail measure.

Multiplex TaqMan assays can be performed using multiple dyes with distinct emission wavelengths. Available dyes for this purpose are FAM, TET, VIC and JOE (the most expensive). TAMRA is reserved as the quencher on the probe and ROX as the passive reference. For best results, the combination of FAM (target) and VIC (endogenous control) is recommended (they have the largest difference in emission maximum) whereas JOE and VIC should not be combined. It is important that if the dye layer has not been chosen correctly, the machine will still read the other dye's spectrum. For example, both VIC and FAM emit fluorescence in a similar range to each other and when doing a single dye, the wells should be labelled correctly. In the case of multiplexing, the spectral compensation for the post run analysis should be turned on (on ABI 7700: Instrument/Diagnostics/Advanced Options/Miscellaneous). Activating spectral compensation improves dye spectral resolution.

Nested PCR

The disclosed methods can further utilize nested PCR. Nested PCR increases the specificity of DNA amplification, by reducing background due to non-specific amplification of DNA. Two sets of primers are being used in two successive PCRs. In the first reaction, one pair of primers is used to generate DNA products, which besides the intended target, may still consist of non-specifically amplified DNA fragments. The product(s) are then used in a second PCR with a set of primers whose binding sites are completely or partially different from and located 3' of each of the primers used in the first reaction. Nested PCR is often more successful in specifically amplifying long DNA fragments than conventional PCR, but it requires more detailed knowledge of the target sequences.

Thus, disclosed herein in one aspect are methods of diagnosing an anaplastic lymphoma kinase (ALK) related cancer in a subject comprising conducting a PCR reaction on DNA from a tissue sample from the subject; wherein the PCR reaction comprises a reverse primer capable of specifically hybridizing to one or more ALK sequences and at least one forward primer; and wherein an increase in the amount of amplification product relative to a control indicates the presence of an ALK related cancer.

Primers and Probes

As used herein, "primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

As used herein, "probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

Disclosed are compositions including primers and probes, which are capable of interacting with the disclosed nucleic acids such as SEQ ID NO: 1 or its complement. In certain embodiments the primers are used to support nucleic acid extension reactions, nucleic acid replication reactions, and/or nucleic acid amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are disclosed. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids. As an example of the use of primers, one or more primers can be used to create extension products from and templated by a first nucleic acid.

The size of the primers or probes for interaction with the nucleic acids can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the nucleic acid of interest typically will be used to produce extension products and/or other replicated or amplified products that contain a region of the nucleic acid of interest. The size of the product can be such that the size can be accurately determined to within 3, or 2 or 1 nucleotides.

In certain embodiments the product can be, for example, at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product can be, for example, less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

Thus, it is understood and herein contemplated that the disclosed RT-PCR and PCR reactions that comprise a portion of the disclosed methods or performed using the disclosed kits require forward and reverse primers to form a primer pair. Herein disclosed, the forward primer can be a primer that specifically hybridizes to an ALK kinase domain such as, for example, SEQ ID NO: 3. The reverse primer can also comprise a primer that specifically hybridizes to the kinase domain of ALK as set forth in SEQ ID NO: 1, such as, for example, the scorpion primer as set forth in SEQ ID NO: 2. Thus, in one aspect, disclosed herein are kits and methods wherein the forward primer is SEQ ID NO: 3 and the reverse primer is SEQ ID NO: 2. For example, in one aspect, disclosed herein are methods of diagnosing a cancer comprising an ALK fusion or assessing the suitability of a ALK kinase directed treatment in a human subject the method comprising performing a Polymerase Chain Reaction (PCR) reaction on the nucleic acid from the tissue sample, wherein the PCR reaction comprises at least one forward primer and at least one reverse primer that specifically hybridizes to a nucleic acid encoding the kinase of ALK as set forth in SEQ ID NO: 1 (such as, for example SEQ ID NO: 3 and SEQ ID NO: 2), and detecting the presence or absence of the kinase domain of ALK, wherein the presence of the kinase domain of ALK indicates the presence of an ALK fusion. It is understood and herein contemplated that other ALK kinase hybridizing forward and reverse primers can be used in the disclosed methods and kits including the forward primers SEQ ID NO: 7, SEQ ID NO: 74, SEQ ID NO: 75, and SEQ ID NO: 90 and the reverse primers SEQ ID NO: 6, SEQ ID NO: 32, SEQ ID NO: 46, SEQ ID NO: 47, SEQ ID NO: 57, SEQ ID NO: 58, SEQ ID NO: 66, and SEQ ID NO: 91. It is further understood that any of the ALK kinase hybridizing forward primers can be used combination with any of the ALK kinase hybridizing reverse primers in performance of the methods disclosed herein.

In one aspect, the disclosed rt-PCR and PCR reactions can comprise additional primer pairs such as, for example, primer pairs that bind to other regions of the ALK kinase domain, the extracellular region of ALK, or ALK fusion junctions created by the fusion of ALK with a fusion partner. For example, disclosed herein are methods of diagnosis and kits comprising a forward primer as set forth in SEQ ID NO: 3, further comprising an intracellular ALK kinase forward primer such as, for example, (primer 100) 5'ACTACT-GCTTTGCTGGCAAGACCT (SEQ ID NO: 7), an extracellular EML4-ALK fusion primer such as, for example, (primer 103) 5'TGTTCAAGATCGCCTGTCAGCTCT (SEQ ID NO: 8); an extracellular NPM-ALK fusion primer such as, for example, (primer 102); 5'TCTGTACAGC-CAACGGTTTCCCTT (SEQ ID NO: 9); an extracellular CTLC-ALK fusion primer such as, for example, (primer 105) 5'GAGAGTGCTTTGGAGCTTGTCTGT (SEQ ID NO: 10); or an extracellular region of wildtype ALK primer from a region of non-homology such as, for example, (primer 104) 5' TTCCTTCATCAGTCCACTGGGCAT (SEQ ID NO: 11). Additional forward and reverse primers that can be used in the methods disclosed herein can be found in Table 4 including, but not limited to Forward primers that bind to the kinase domain of ALK such as, for example, SEQ ID NO:7, SEQ ID NO: 74, SEQ ID NO: 75, and SEQ ID NO: 90.

The reverse primer can be, for example, SEQ ID NO: 2. In one aspect the kits and methods disclosed herein can further comprise additional ALK kinase reverse primers such as, for example, primer 101: 5' TCGTCCTGTTCA- GAGCACACTTCA (SEQ ID NO: 6). Alternatively, methods and kits disclosed herein can comprise the reverse primer as set forth in SEQ ID NO: 2 and further comprise SEQ ID NO: 6, SEQ ID NO: 32, SEQ ID NO: 46, SEQ ID NO: 47, SEQ ID NO: 57, SEQ ID NO: 58, SEQ ID NO: 66, or SEQ ID NO: 91. It is understood and herein contemplated that the disclosed ALK kinase reverse primer of SEQ ID NO: 2 can be substituted for any suitable reverse primer that specifically hybridizes to an ALK kinase domain including but not limited to SEQ ID NO: 6, SEQ ID NO: 32, SEQ ID NO: 46, SEQ ID NO: 47, SEQ ID NO: 57, SEQ ID NO: 58, SEQ ID NO: 66, or SEQ ID NO: 91. Thus, in one aspect, disclosed herein are kits and methods wherein the reverse primer comprises SEQ ID NO: 6, SEQ ID NO: 32, SEQ ID NO: 46, SEQ ID NO: 47, SEQ ID NO: 57, SEQ ID NO: 58, SEQ ID NO: 66 or SEQ ID NO: 91.

It is understood that the methods and kits disclosed herein comprise at least one forward primer and a reverse primer. Thus, disclosed herein are methods of diagnosing an anaplastic lymphoma kinase (ALK) related cancer in a subject comprising conducting an RT-PCR reaction on mRNA from a tissue sample from the subject; wherein the reverse transcription polymerase chain reaction (RT-PCR) comprises a forward and reverse primer pair capable of specifically hybridizing the ALK kinase domain. The method can further comprise a reverse primer that specifically hybridizes to one or more ALK sequences (for example an ALK kinase domain or an ALK extracellular region) and at least one forward primer; wherein the forward primer is selected from the group consisting of ALK extracellular region forward primer, ALK kinase domain forward primer, KIF5B-ALK primer, NPM-ALK primer, ALK-ALK primer, CLTC-ALK primer, RANBP2-ALK primer, SEC31L1-ALK primer, TPM3-ALK primer, TPM4-ALK primer, $TFG_L$-ALK primer, $TFG_S$-ALK primer, CARS-ALK primer, EML4-ALK primer, ALO17-ALK primer, MYH9-ALK primer, MSN-ALK primer, and $TFG_{XL}$-ALK primer; and wherein an increase in the amount of amplification product or the presence of amplification product indicates the presence of an ALK related cancer. It is understood that in some instances a negative control sample can be used in the disclosed methods and kits. Thus, the increase or presence of the ALK amplification product can be determined relative to a control.

It is understood and herein contemplated that there are situations where it may be advantageous to utilize more than one primer pair to detect the presence of a fusion, truncation, or over expression mutation. Such RT-PCR or PCR reactions can be conducted separately, or in a single reaction. When multiple primer pairs are placed into a single reaction, this is referred to as "multiplex PCR." For example, the reaction can comprise a ALK kinase forward and reverse primer pair, as well as, an ALK fusion forward primer or ALK extracellular region forward primer paired with the same reverse primer. Thus, disclosed herein are methods of diagnosing an anaplastic lymphoma kinase (ALK) related cancer in a subject comprising conducting an RT-PCR reaction on mRNA from a tissue sample from the subject; wherein the reverse transcription polymerase chain reaction (RT-PCR) comprises a reverse primer capable of specifically hybridizing to one or more ALK kinase sequences and one or more forward primers; and wherein the presence of or an increase in the amount of amplification product indicates the presence of an ALK related cancer.

Fluorescent Change Probes and Primers

Fluorescent change probes and fluorescent change primers refer to all probes and primers that involve a change in fluorescence intensity or wavelength based on a change in the form or conformation of the probe or primer and nucleic acid to be detected, assayed or replicated. Examples of fluorescent change probes and primers include molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, PNA probes and QPNA probes.

Fluorescent change probes and primers can be classified according to their structure and/or function. Fluorescent change probes include hairpin quenched probes, cleavage quenched probes, cleavage activated probes, and fluorescent activated probes. Fluorescent change primers include stem quenched primers and hairpin quenched primers.

Hairpin quenched probes are probes that when not bound to a target sequence form a hairpin structure (and, typically, a loop) that brings a fluorescent label and a quenching moiety into proximity such that fluorescence from the label is quenched. When the probe binds to a target sequence, the stem is disrupted, the quenching moiety is no longer in proximity to the fluorescent label and fluorescence increases. Examples of hairpin quenched probes are molecular beacons, fluorescent triplex oligos, triplex molecular beacons, triplex FRET probes, and QPNA probes.

Cleavage activated probes are probes where fluorescence is increased by cleavage of the probe. Cleavage activated probes can include a fluorescent label and a quenching moiety in proximity such that fluorescence from the label is quenched. When the probe is clipped or digested (typically by the 5'-3' exonuclease activity of a polymerase during amplification), the quenching moiety is no longer in proximity to the fluorescent label and fluorescence increases. TaqMan probes are an example of cleavage activated probes.

Cleavage quenched probes are probes where fluorescence is decreased or altered by cleavage of the probe. Cleavage quenched probes can include an acceptor fluorescent label and a donor moiety such that, when the acceptor and donor are in proximity, fluorescence resonance energy transfer from the donor to the acceptor causes the acceptor to fluoresce. The probes are thus fluorescent, for example, when hybridized to a target sequence. When the probe is clipped or digested (typically by the 5'-3' exonuclease activity of a polymerase during amplification), the donor moiety is no longer in proximity to the acceptor fluorescent label and fluorescence from the acceptor decreases. If the donor moiety is itself a fluorescent label, it can release energy as fluorescence (typically at a different wavelength than the fluorescence of the acceptor) when not in proximity to an acceptor. The overall effect would then be a reduction of acceptor fluorescence and an increase in donor fluorescence. Donor fluorescence in the case of cleavage quenched probes is equivalent to fluorescence generated by cleavage activated probes with the acceptor being the quenching moiety and the donor being the fluorescent label. Cleavable FRET (fluorescence resonance energy transfer) probes are an example of cleavage quenched probes.

Fluorescent activated probes are probes or pairs of probes where fluorescence is increased or altered by hybridization of the probe to a target sequence. Fluorescent activated probes can include an acceptor fluorescent label and a donor moiety such that, when the acceptor and donor are in proximity (when the probes are hybridized to a target sequence), fluorescence resonance energy transfer from the donor to the acceptor causes the acceptor to fluoresce. Fluorescent activated probes are typically pairs of probes designed to hybridize to adjacent sequences such that the acceptor and donor are brought into proximity Fluorescent activated probes can also be single probes containing both a donor and acceptor where, when the probe is not hybridized to a target sequence, the donor and acceptor are not in proximity but where the donor and acceptor are brought into proximity when the probe hybridized to a target sequence. This can be accomplished, for example, by placing the donor and acceptor on opposite ends of the probe and placing target complement sequences at each end of the probe where the target complement sequences are complementary to adjacent sequences in a target sequence. If the donor moiety of a fluorescent activated probe is itself a fluorescent label, it can release energy as fluorescence (typically at a different wavelength than the fluorescence of the acceptor) when not in proximity to an acceptor (that is, when the probes are not hybridized to the target sequence). When the probes hybridize to a target sequence, the overall effect would then be a reduction of donor fluorescence and an increase in acceptor fluorescence. FRET probes are an example of fluorescent activated probes.

Stem quenched primers are primers that when not hybridized to a complementary sequence form a stem structure (either an intramolecular stem structure or an intermolecular stem structure) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. In the disclosed method, stem quenched primers are used as primers for nucleic acid synthesis and thus become incorporated into the synthesized or amplified nucleic acid. Examples of stem quenched primers are peptide nucleic acid quenched primers and hairpin quenched primers.

Peptide nucleic acid quenched primers are primers associated with a peptide nucleic acid quencher or a peptide nucleic acid fluor to form a stem structure. The primer contains a fluorescent label or a quenching moiety and is associated with either a peptide nucleic acid quencher or a peptide nucleic acid fluor, respectively. This puts the fluorescent label in proximity to the quenching moiety. When the primer is replicated, the peptide nucleic acid is displaced, thus allowing the fluorescent label to produce a fluorescent signal.

Hairpin quenched primers are primers that when not hybridized to a complementary sequence form a hairpin structure (and, typically, a loop) that brings a fluorescent label and a quenching moiety into proximity such that fluorescence from the label is quenched. When the primer binds to a complementary sequence, the stem is disrupted, the quenching moiety is no longer in proximity to the fluorescent label and fluorescence increases. Hairpin quenched primers are typically used as primers for nucleic acid synthesis and thus become incorporated into the synthesized or amplified nucleic acid. Examples of hairpin quenched primers are Amplifluor primers and scorpion primers.

Cleavage activated primers are similar to cleavage activated probes except that they are primers that are incorporated into replicated strands and are then subsequently cleaved.

Labels

To aid in detection and quantitation of nucleic acids produced using the disclosed methods, labels can be directly incorporated into nucleotides and nucleic acids or can be coupled to detection molecules such as probes and primers. As used herein, a label is any molecule that can be associated with a nucleotide or nucleic acid, directly or indirectly, and which results in a measurable, detectable signal, either directly or indirectly. Many such labels for incorporation into nucleotides and nucleic acids or coupling to nucleic acid probes are known to those of skill in the art. Examples of labels suitable for use in the disclosed method are radioactive isotopes, fluorescent molecules, phosphorescent molecules, enzymes, antibodies, and ligands. Fluorescent labels, especially in the context of fluorescent change probes and primers, are useful for real-time detection of amplification.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, CASCADE BLUE®, OREGON GREEN®, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine 0, Coumarin-Phalloidin, CY3.18, CY5.18, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow SGF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin EBG, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Phycoerythrin B, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

The absorption and emission maxima, respectively, for some of these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037 which is incorporated herein by reference.

Labeled nucleotides are a form of label that can be directly incorporated into the amplification products during synthesis. Examples of labels that can be incorporated into amplified nucleic acids include nucleotide analogs such as BrdUrd, aminoallyldeoxyuridine, 5-methylcytosine, bromouridine, and nucleotides modified with biotin or with suitable haptens such as digoxygenin. Suitable fluorescence-labeled nucleotides are Fluorescein-isothiocyanate-dUTP, Cyanine-3-dUTP and Cyanine-5-dUTP. One example of a nucleotide analog label for DNA is BrdUrd (bromodeoxyuridine, BrdUrd, BrdU, BUdR, Sigma-Aldrich Co). Other examples of nucleotide analogs for incorporation of label into DNA are AA-dUTP (aminoallyl-deoxyuridine triphosphate, Sigma-Aldrich Co.), and 5-methyl-dCTP (Roche Molecular Biochemicals). One example of a nucleotide analog for incorporation of label into RNA is biotin-16-UTP (biotin-16-uridine-5'-triphosphate, Roche Molecular Biochemicals). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl) phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Molecules that combine two or more of these labels are also considered labels. Any of the known labels can be used with the disclosed probes, tags, and method to label and detect nucleic acid amplified using the disclosed method. Methods for detecting and measuring signals generated by labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary label coupled to the antibody. As used herein, detection molecules are molecules which interact with amplified nucleic acid and to which one or more labels are coupled.

It is understood and herein contemplated that one method of assessing whether an increase in a particular mRNA or expression of mRNA has occurred or a particular mRNA is present is by comparison with a control sample. Therefore, contemplated herein are methods of diagnosing a cancer in a subject comprising conducting an RT-PCR or PCR reaction with mRNA from a tissue sample from the subject; wherein the reverse transcription polymerase chain reaction (RT-PCR) comprises a reverse primer capable of specifically hybridizing to one or more ALK kinase domain sequences as set forth in SEQ ID NO: 1 and at least one forward primer; wherein an increase in the amount of amplification product relative to a control indicates the presence of an ALK related cancer; and wherein the control tissue is obtained is a non-cancerous tissue. It is further understood that with respect to ALK-related cancers, the use of a non-cancerous tissue control can be utilized but is not necessary as cancerous tissue from a non-ALK related cancer may also be used. Thus, disclosed herein are diagnosing an anaplastic lymphoma kinase (ALK) related cancer (such as, for example, a cancer comprising an ALK fusion) in a subject comprising conducting an RT-PCR reaction on mRNA from a tissue sample from the subject; wherein the reverse transcription polymerase chain reaction (RT-PCR) comprises a reverse primer capable of specifically hybridizing to one or more ALK kinase domain sequences and at least one forward primer that specifically hybridizes to one or more ALK kinase domain sequences; and wherein an increase in the amount of amplification product relative to a control indicates the presence of an ALK related cancer; and wherein the control tissue is obtained from non-ALK related cancerous tissue.

The disclosed methods can be used to diagnose any disease where uncontrolled cellular proliferation occurs herein referred to as "cancer". A non-limiting list of different types of ALK related cancers is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumours, myelomas, AIDS-related lymphomas or sarcomas, metastatic cancers, or cancers in general.

A representative but non-limiting list of cancers that the disclosed methods can be used to diagnose is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

Thus, disclosed herein are methods of diagnosing a cancer wherein the cancer is selected from the group consisting of non-small cell lung carcinoma, diffuse large B-cell lymphoma, systemic histiocytosis, breast cancer, colorectal carcinoma, esophageal squamous cell carcinoma, anaplastic large-cell lymphoma, neuroblastoma, and inflammatory myofibroblastic tumors (IMTs). For example, disclosed herein are methods of diagnosing an anaplastic lymphoma kinase (ALK) related cancer in a subject comprising conducting an RT-PCR reaction on mRNA from a tissue sample from the subject; wherein the reverse transcription polymerase chain reaction (RT-PCR) comprises a reverse primer capable of specifically hybridizing to one or more ALK sequences and at least one forward primer; wherein an increase in the amount of amplification product relative to a control indicates the presence of an ALK related cancer, and wherein the cancer is selected from the group consisting of non-small cell lung carcinoma, diffuse large B-cell lymphoma, systemic histiocytosis, breast cancer, colorectal carcinoma, esophageal squamous cell carcinoma, anaplastic large-cell lymphoma, neuroblastoma, and inflammatory myofibroblastic tumors (IMTs).

Methods of Assessing the Suitability of ALK Directed Treatments

Though not wishing to be bound by current theories, it is believed that inhibition of these forms of ALK genes with small-molecule drug candidates abrogates related abnormal cell proliferation and promotes apoptosis in neuroblastoma and other ALK-related tumor cell lines; furthermore, both preclinical animal models and the early clinical experience with these inhibitors indicate that ALK small-molecule inhibitors not only possess marked antitumor activity against ALK-related cancers but are also very well tolerated with no limiting target-associated toxicities.

These discoveries highlight the need for a specialized diagnostic test for ALK mutations. For example, such an assay may be used to screen children in families affected with hereditary neuroblastoma to help facilitate the detection of tumors at an earlier stage when the tumors are more amenable to treatment. Accordingly, disclosed herein are methods of assessing the suitability of an ALK inhibitor treatment for a cancer in a subject comprising measuring mRNA from a tissue sample from the subject; wherein an increase in the amount of ALK sequence mRNA relative to a control indicates a cancer that can be treated with an ALK inhibitor.

It is understood and herein contemplated that any of the disclosed mRNA measuring techniques disclosed herein can be used in these methods. Thus, for example, disclosed herein are methods of assessing the suitability of an ALK inhibitor treatment for a cancer in a subject comprising conducting an RT-PCR reaction with mRNA or PCR reaction with DNA from a tissue sample from the subject; wherein the RT-PCR reaction comprises a reverse primer capable of specifically hybridizing to one or more ALK kinase domain sequences and at least one forward primer capable of specifically hybridizing to one or more ALK kinase sequences; and wherein an increase in the amount of amplification product relative to a control or the presence of amplification produce indicates a cancer that can be treated with an ALK inhibitor. It is further understood that the disclosed methods can further comprise any of the primers disclosed herein and utilize the multiplexing PCR techniques disclosed. Once a determination that the cancer can be treated with an ALK inhibitor is made by detection of an ALK amplification product, the method can further comprise treating the subject with an ALK kinase inhibitor. Where a determination is made that the ALK inhibitor is not suitable for treatment, the method can further comprise administering a treatment regimen that does not include an ALK inhibitor. Thus, in one aspect, disclosed herein are methods of treating a cancer comprising an ALK fusion or dysregulation of ALK (e.g., ALk overexpression) comprising conducting a nucleic acid amplification process on a tissue sample from the subject and detecting the presence of nucleic acid associated with the ALK kinase domain in the tissue sample, wherein the presence of nucleic acid associated with the ALK kinase domain indicates a cancer comprising an ALK fusion or ALK overexpression; and administering an ALK inhibitor to the subject.

Methods of Screening

The ALK-fusions and point mutations disclosed herein are targets for cancer treatments. Thus, disclosed herein are method of screening for an agent that inhibits a cancer comprising an ALK fusion comprising a) obtaining a tissue sample with a cancer comprising an ALK fusion;
b) contacting the tissue sample with the agent
c) extracting nucleic acid from the tissue sample;
d) conducting a PCR, RT-PCR, real-time PCR, or real-time RT-PCR reaction on the mRNA from the tissue sample;

wherein the reaction comprises a forward and reverse primer pair that specifically hybridizes to ALK kinase domain as set forth in SEQ ID NO: 1; and wherein a decrease in the amount of amplification product relative to an untreated control indicates an agent that can inhibit a cancer comprising an ALK fusion.

Nucleic Acids

The disclosed method and compositions make use of various nucleic acids. Generally, any nucleic acid can be used in the disclosed method. For example, the disclosed nucleic acids of interest and the disclosed reference nucleic acids can be chosen based on the desired analysis and information that is to be obtained or assessed. The disclosed methods also produce new and altered nucleic acids. The nature and structure of such nucleic acids will be established by the manner in which they are produced and manipulated in the methods. Thus, for example, extension products and hybridizing nucleic acids are produced in the disclosed methods. As used herein, hybridizing nucleic acids are hybrids of extension products and the second nucleic acid.

It is understood and contemplated herein that a nucleic acid of interest can be any nucleic acid to which the determination of the presence or absence of nucleotide variation is desired. Thus, for example, the nucleic acid of interest can comprise a sequence that corresponds to the wild-type sequence of the reference nucleic acid. It is further disclosed herein that the disclosed methods can be performed where the first nucleic acid is a reference nucleic acid and the second nucleic acid is a nucleic acid of interest or where the first nucleic acid is the nucleic acid of interest and the second nucleic acid is the reference nucleic acid.

It is understood and herein contemplated that a reference nucleic acid can be any nucleic acid against which a nucleic acid of interest is to be compared. Typically, the reference nucleic acid has a known sequence (and/or is known to have a sequence of interest as a reference). Although not required, it is useful if the reference sequence has a known or suspected close relationship to the nucleic acid of interest. For example, if a single nucleotide variation is desired to be detected, the reference sequence can be usefully chosen to be a sequence that is a homolog or close match to the nucleic acid of interest, such as a nucleic acid derived from the same gene or genetic element from the same or a related organism or individual. Thus, for example, it is contemplated herein that the reference nucleic acid can comprise a wildtype sequence or alternatively can comprise a known mutation including, for example, a mutation the presence or absence of which is associated with a disease or resistance to therapeutic treatment. Thus, for example, it is contemplated that the disclosed methods can be used to detect or diagnose the presence of known mutations in a nucleic acid of interest by comparing the nucleic acid of interest to a reference nucleic acid that comprises a wildtype sequence (i.e., is known not to possess the mutation) and examining for the presence or absence of variation in the nucleic acid of interest, where the absence of variation would indicate the absence of a mutation. Alternatively, the reference nucleic acid can possess a known mutation. Thus, for example, it is contemplated that the disclosed methods can be used to detect susceptibility for a disease or condition by comparing the nucleic acid of interest to a reference nucleic acid comprising a known mutation that indicates susceptibility for a disease and examining for the presence or absence of the mutation, wherein the presence of the mutation indicates a disease.

Herein, the term "nucleotide variation" refers to any change or difference in the nucleotide sequence of a nucleic acid of interest relative to the nucleotide sequence of a reference nucleic acid. Thus, a nucleotide variation is said to occur when the sequences between the reference nucleic acid and the nucleic acid of interest (or its complement, as appropriate in context) differ. Thus, for example, a substitution of an adenine (A) to a guanine (G) at a particular position in a nucleic acid would be a nucleotide variation provided the reference nucleic acid comprised an A at the corresponding position. It is understood and herein contemplated that the determination of a variation is based upon the reference nucleic acid and does not indicate whether or not a sequence is wildtype. Thus, for example, when a nucleic acid with a known mutation is used as the reference nucleic acid, a nucleic acid not possessing the mutation (including a wildtype nucleic acid) would be considered to possess a nucleotide variation (relative to the reference nucleic acid).

Nucleotides

The disclosed methods and compositions make use of various nucleotides. Throughout this application and the methods disclosed herein reference is made to the type of base for a nucleotide. It is understood and contemplated herein that where reference is made to a type of base, this refers a base that in a nucleotide in a nucleic acid strand is capable of hybridizing (binding) to a defined set of one or more of the canonical bases. Thus, for example, where reference is made to extension products extended in the presence of three types of nuclease resistant nucleotides and not in the presence of nucleotides that comprise the same type of base as the modified nucleotides, this means that if, for example, the base of the modified nucleotide was an adenine (A), the nuclease-resistant nucleotides can be, for example, guanine (G), thymine (T), and cytosine (C). Each of these bases (which represent the four canonical bases) is capable of hybridizing to a different one of the four canonical bases and thus each qualify as a different type of base as defined herein. As another example, inosine base pairs primarily with adenine and cytosine (in DNA) and thus can be considered a different type of base from adenine and from cytosine-which base pair with thymine and guanine, respectively—but not a different type of base from guanine or thymine—which base pair with cytosine and adenine, respectively-because the base pairing of guanine and thymine overlaps (that is, is not different from) the hybridization pattern of inosine.

Any type of modified or alternative base can be used in the disclosed methods and compositions, generally limited only by the capabilities of the enzymes used to use such bases. Many modified and alternative nucleotides and bases are known, some of which are described below and elsewhere herein. The type of base that such modified and alternative bases represent can be determined by the pattern of base pairing for that base as described herein. Thus for example, if the modified nucleotide was adenine, any analog, derivative, modified, or variant base that based pairs primarily with thymine would be considered the same type of base as adenine. In other words, so long as the analog, derivative, modified, or variant has the same pattern of base pairing as another base, it can be considered the same type of base. Modifications can made to the sugar or phosphate groups of a nucleotide. Generally such modifications will not change the base pairing pattern of the base. However, the base pairing pattern of a nucleotide in a nucleic acid strand determines the type of base of the base in the nucleotide.

Modified nucleotides to be incorporated into extension products and to be selectively removed by the disclosed agents in the disclosed methods can be any modified nucleotide that functions as needed in the disclosed method as is described elsewhere herein. Modified nucleotides can also be produced in existing nucleic acid strands, such as extension products, by, for example, chemical modification, enzymatic modification, or a combination.

Many types of nuclease-resistant nucleotides are known and can be used in the disclosed methods. For example, nucleotides have modified phosphate groups and/or modified sugar groups can be resistant to one or more nucleases. Nuclease-resistance is defined herein as resistance to removal from a nucleic acid by any one or more nucleases. Generally, nuclease resistance of a particular nucleotide can be defined in terms of a relevant nuclease. Thus, for example, if a particular nuclease is used in the disclosed method, the nuclease-resistant nucleotides need only be resistant to that particular nuclease. Examples of useful nuclease-resistant nucleotides include thio-modified nucleotides and borano-modified nucleotides.

There are a variety of molecules disclosed herein that are nucleic acid based. Non-limiting examples of these and other molecules are discussed herein. It is understood that for example, a nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (adenine, A), cytosin-1-yl (cytosine, C), guanin-9-yl (guanine, G), uracil-1-yl (uracil, U), and thymin-1-yl (thymine, T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil- 5-yl (ψ), hypoxanthin-9-yl (inosine, I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, which is incorporated herein in its entirety for its teachings of base modifications. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[(CH2)n O]m CH3, —O(CH2)n OCH3, —O(CH2)n NH2, —O(CH2)n CH3, —O(CH2)n-ONH2, and —O(CH2)nON[(CH2)n CH3)]2, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2 CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH2 and S. Nucleotide sugar analogs may also have sugar mimetics such as cyclobutyl moieties in place of the pentofuranosyl sugar.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

It is also understood in a nucleotide substitute that both the sugar and the phosphate moieties of the nucleotide can be replaced, by for example an amide type linkage (aminoethylglycine) (PNA).

It is also possible to link other types of molecules (conjugates) to nucleotides or nucleotide analogs. Conjugates can be chemically linked to the nucleotide or nucleotide analogs. Such conjugates include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or 0) at the C6 position of purine nucleotides.

Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

Kits

Disclosed herein are kits that are drawn to reagents that can be used in practicing the methods disclosed herein. In particular, the kits can include any reagent or combination of reagents discussed herein or that would be understood to be required or beneficial in the practice of the disclosed methods. For example, the kits could include one or more primers disclosed herein to perform the extension, replication and amplification reactions discussed in certain embodiments of the methods, as well as the buffers and enzymes required to use the primers as intended.

It is understood that to detect an ALK related fusion, a reverse primer can be used that hybridizes with the kinase domain of ALK. Thus, disclosed herein are kits that include at least one reverse primer wherein the reverse primer hybridizes to a portion of the kinase domain of wild-type ALK as set forth in SEQ ID NO: 1 (such as, for example, exons 21, 22, 23, 24, 25, or 26 of ALK). For example, in one aspect, the reverse primer can specifically hybridize to exon 24 or exon 26 of ALK as set forth in SEQ ID NO: 1. Examples of reverse primers that can be used in the disclosed kits include but are not limited to SEQ ID NO: 2. Additional reverse primers for the disclosed kits can comprise, for example, SEQ ID NO: 6, SEQ ID NO: 32, SEQ ID NO: 46, SEQ ID NO: 47, SEQ ID NO: 57, SEQ ID NO: 58, SEQ ID NO: 66, and SEQ ID NO: 91. Additionally, it is understood that the kits disclosed herein can include one or more forward primers that specifically hybridize to the ALK kinase domain as set forth in SEQ ID NO: 1. (such as, for example, exons 21, 22, 23, 24, 25, or 26 of ALK). For example, in one aspect, the forward primer can specifically hybridize to exon 24 or exon 26 of ALK as set forth in SEQ ID NO: 1. Examples of other forward primers that can be used in the disclosed kits include but are not limited to SEQ ID NO: 3, SEQ ID NO: 7, SEQ ID NO: 74, SEQ ID NO: 75, and SEQ ID NO: 90.

In one aspect, it is understood that advantages can be obtained through the inclusion of additional primers, the disclosed kits can further comprise forward and/or reverse primers that specifically hybridize to additional portions of the ALK kinase domain (for example SEQ ID NO: 6, SEQ ID NO: 7, SEQ ID NO: 32, SEQ ID NO: 46, SEQ ID NO: 47, SEQ ID NO: 57, SEQ ID NO: 58, SEQ ID NO: 66, SEQ ID NO: 74, SEQ ID NO: 75, SEQ ID NO: 90, or SEQ ID NO: 91), a fusion partner of ALK, or wild-type ALK (see, for example, SEQ ID NO: 61, SEQ ID NO: 81, SEQ ID NO: 82, SEQ ID NO: 89). Examples listed in Table 4 could all be used in the disclosed kits. Thus, for example the kits can comprise a forward primer that can specifically hybridize to the extracellular region of ALK, the kinase domain of ALK, 5-aminoimidazole-4-carboxamide ribonucleotide formyltransferase/IMP cyclohydrolase (ATIC), clathrin heavy chain (CLTC), Ran-binding protein 2 (RANBP2), SEC31L1, tropomyosin-3 (TPM3), tropomyosin-4 (TPM4), TRK-fused gene(Large) (TFG$_L$), TRK-fused gene(Small) (TFG$_S$), CARS, ALO17, moesin (MSN), non-muscle myosin heavy chain gene (MYH9), or TRK-fused gene(Extra Large) (TFG$_{XL}$). The disclosed kits can also further comprise one or more additional reverse primer such as those listed in Table 4 to form a primer pair with the additional forward primer (such as, for example, a reverse primer that specifically hybridizes to the extracellular region of ALK which can be paired with a forward primer that hybridizes to the same region). A non-limiting list of additional forward and reverse primers that can be used in the kits disclosed herein include those specifically disclosed herein and the primers listed in Table 4. One of skill in the art can appreciate that it is suitable to have a kit that comprises more than a singular primer pair and could include, for example, a single reverse primer, such as SEQ ID NO: 2, and multiple forward primers. Thus, specifically contemplated herein are kits including a forward primer that specifically hybridizes to the kinase domain of ALK (such as, for example, SEQ ID NO: 3) and one or more forward primers that specifically hybridizes to the extracellular region of ALK, 5-aminoimidazole-4-carboxamide ribonucleotide formyltransferase/IMP cyclohydrolase (ATIC), clathrin heavy chain (CLTC), Ran-binding protein 2 (RANBP2), SEC31L1, tropomyosin-3 (TPM3), tropomyosin-4 (TPM4), TRK-fused gene (Large) (TFG$_L$), TRK-fused gene(Small) (TFG$_S$), CARS, ALO17, moesin (MSN), non-muscle myosin heavy chain gene (MYH9), or TRK-fused gene(Extra Large) (TFG$_{XL}$) and at least one reverse primer, wherein the reverse primer is specifically hybridizes to the ALK kinase domain, such as, for example SEQ ID NO: 2.

In one aspect, the disclosed forward and/or reverse primers can be a scorpion primer such as, for example a unimolecular scorpion probe and primer, such as, for example, SEQ ID NO: 2.

It is understood that the disclosed kits can also include controls to insure the methods disclosed herein are properly functioning and to normalize results between assays. Thus, for example, disclosed herein are positive cDNA controls, negative cDNA controls, and control primer pairs. For example, the disclosed kits can include a control primer pairs for the detection of ABL, *Homo sapiens* ATP synthase, H+ transporting, mitochondrial F1 complex, O subunit (ATP5O), nuclear gene encoding mitochondrial protein mRNA; *Homo sapiens* NADH dehydrogenase (ubiquinone) 1 alpha subcomplex, 2, 8 kDa (NDUFA2), mRNA; *Homo sapiens* glyceraldehyde-3-phosphate dehydrogenase (GAPDH), mRNA; *Homo sapiens* H3 histone, family 3A (H3F3A), mRNA; *Homo sapiens* proteasome (prosome, macropain) subunit, beta type, 4 (PSMB4), mRNA; *Homo sapiens* ribosomal protein S27a (RPS27A), transcript variant 1, mRNA; *Homo sapiens* eukaryotic translation initiation factor 4A, isoform 2 (EIF4A2), mRNA; *Homo sapiens* ribosomal protein L18 (RPL18), mRNA; *Homo sapiens* adenosine deaminase, RNA-specific (ADAR), transcript variant 1, mRNA; or *Homo sapiens* cytochrome c oxidase subunit Vb (COX5B), mRNA. Examples of primers pairs include but are not limited to the primer pairs found in Table 1.

TABLE 1

| Sequence Name | Forward Primer | Reverse Primer |
|---|---|---|
| ABL | GCAGCTCCTTGGGGTCTGC (SEQ ID NO: 5) | (FAM)-ACGCGCCTACGGGAACCTCCTGGCGCGT-(Dabcyl-dT)-(Sp18)-CGGTTGCACTCCCTCAGGTA (SEQ ID NO: 4) |
| ATP5O | GCGTTTCTCTCTTCCCACTC (SEQ ID NO: 12) | GGCATAGCGACCTTCAATACC (SEQ ID NO: 22) |
| NDUFA2 | GCCTGAAGACCTGGAATTGG (SEQ ID NO: 13) | CTGACATAAGTGGATGCGAATC (SEQ ID NO: 23) |
| GAPDH | GGAAGGTGAAGGTCGGAGTC (SEQ ID NO: 14) | GCTGATGATCTTGAGGCTGTTG (SEQ ID NO: 24) |
| H3F3A | CCAGCCGAAGGAGAAGGG (SEQ ID NO: 15) | AGGGAAGTTTGCGAATCAGAAG (SEQ ID NO: 25) |
| PSMB4 | TACCGCATTCCGTCCACTC (SEQ ID NO: 16) | GCTCCTCATCAATCACCATCTG (SEQ ID NO: 26) |
| RPS27A | CGGCAGTCAGGCATTTGG (SEQ ID NO: 17) | CCACCACGAAGTCTCAACAC (SEQ ID NO: 27) |
| EIF4A2 | CTCTCCTTCGTGGCATCTATG (SEQ ID NO: 18) | GGTCTCCTTGAACTCAATCTCC (SEQ ID NO: 28) |
| RPL18 | GGACATCCGCCATAACAAGG (SEQ ID NO: 19) | ACAACCTCTTCAACACAACCTG (SEQ ID NO: 29) |
| ADAR | AGACGGTCATAGCCAAGGAG (SEQ ID NO: 20) | GCAGAGGAGTCAGACACATTG (SEQ ID NO: 30) |
| COX5B | ACGCAATGGCTTCAAGGTTAC (SEQ ID NO: 21) | CGCTGGTATTGTCCTCTTCAC (SEQ ID NO: 31) |

In one aspect, disclosed herein are kits comprising a forward and reverse primer pair that specifically hybridizes to the kinase domain of ALK (such as, for example, SEQ ID NO: 3 and 2) and a control primer pair that specifically hybridizes to ABL (such as, for example SEQ ID NO: 5 and 4) as shown in Table 2.

TABLE 2

| Primer Name | Flourophor | Blocker | Sequence (5'-3') |
| --- | --- | --- | --- |
| ALK-R | FAM | BHQ1 | (FAM)-ccgcgcCACTTCATCCACCGAGACATTGCgcgcgg-(BHQ1)-(Sp18)-GGACAGGTCAAGAGGCAGTTTCT (SEQ ID NO: 2) |
| ALK-F | none | none | TTCTGCACGTGGCTCGGGACATT (SEQ ID NO: 3) |
| ABL-R | FAM | Dabcyl-dT | (FAM)-ACGCGCCTACGGGAACCTCCTGGCGCGT-(Dabcyl-dT)-(Sp18)-CGGTTGCACTCCCTCAGGTA (SEQ ID NO: 4) |
| ABL-F | none | none | GCAGCTCCTTGGGGTCTGC (SEQ ID NO: 5) |

Additionally, it is understood that the disclosed kits can include such other reagents and material for performing the disclosed methods such as an enzymes (e.g., polymerases), buffers, sterile water, reaction tubes. Additionally the kits can also include modified nucleotides, nuclease-resistant nucleotides, and or labeled nucleotides. Additionally, the disclosed kits can include instructions for performing the methods disclosed herein and software for enable the calculation of the presence of an ALK mutation.

In one aspect, the disclosed kits can comprise sufficient material in a single assay run simultaneously or separately to conduct the methods to determine if a sample contains a wildtype ALK, a known ALK fusion, or a previously unidentified ALK fusion. The kits can also include sufficient material to run control reactions. Thus, disclosed herein, in one aspect, are kits comprising a positive cDNA or mRNA control reaction tube, a negative cDNA c or mRNA control reaction tube, a control primer reaction tube, and a reaction tube to detect ALK kinase thereby detecting the presence of an ALK fusion or aberrant ALK expression (i.e., overexpression).

In another configuration, the disclosed kit can be used to determine ALK status—either wildtype expression, kinase domain overexpression, or fusion mutation overexpression—on the basis of measurements made relative to internal control genes. The internal control genes, described elsewhere in this disclosure, are understood to be expressed stably and constitutively irrespective of cell cycle, development or environmental factors. Therefore, in one aspect, ALK status can be determined via an equation of ALK (numerator)/internal control (denominator) where the resulting quotient is a range of outcomes that indicate tested tissues, cell lines or other samples are either ALK positive or ALK negative. With an understanding that certain tissues express internal control transcripts at different levels, the ratio and quotient determined to indicate ALK positive or negative status will be established separately for each tissue and specimen type.

The compositions disclosed herein and the compositions necessary to perform the disclosed methods can be made using any method known to those of skill in the art for that particular reagent or compound unless otherwise specifically noted.

Nucleic Acid Synthesis

The disclosed nucleic acids, such as, the oligonucleotides to be used as primers can be made using standard chemical synthesis methods or can be produced using enzymatic methods or any other known method. Such methods can range from standard enzymatic digestion followed by nucleotide fragment isolation to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B).

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Example 1

ALK Fusion Genes in Hematological Malignancies and Solid Tumors (Anaplastic Large-Cell Lymphoma, ALK+ Diffuse Large B-Cell Lymphoma, ALK+ Systemic Histiocytosis, IMT Sarcoma, Non-Small Cell Lung Carcinoma, Esophageal Squamous Cell Carcinoma, Breast Cancer, Colorectal Carcinoma)

Figure 3:
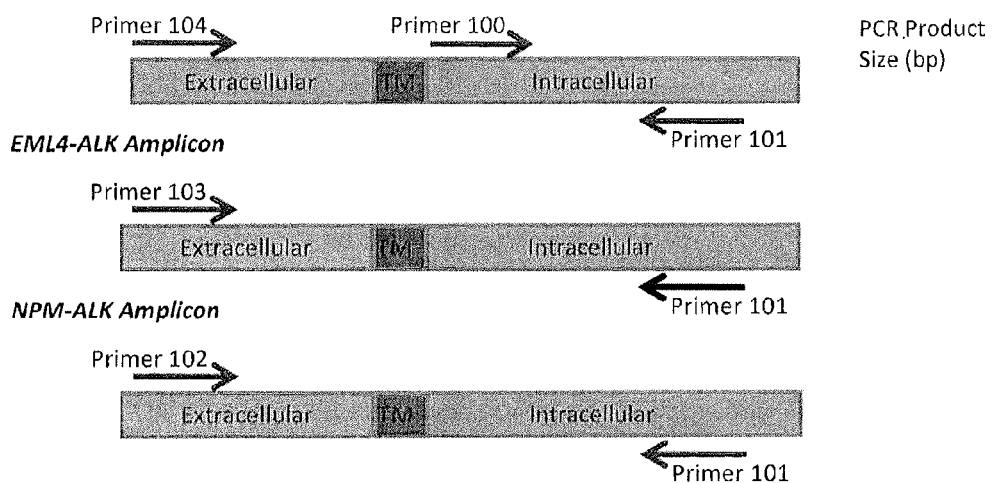
FIG. 3 shows approximate primer and probe positions for the forward and reverse ALK scorpion primer pair.

Although the point mutations of ALK occur in neuroblastoma, so-called "ALK fusions" actually represent the most common mutation of this tyrosine kinase (FIG. 1). Subsets of each of the hematological (blood system-derived) and solid tumors listed above in the heading are caused by ALK fusions. As one example, the novel EML4-ALK fusion protein is found in nearly 7% of Japanese non-small cell lung carcinoma patients. To perform RT-PCR detection of ALK fusion sequences, tissue samples from a subject with a cancer are obtained. mRNA is extracted from the tissue samples. The RT-PCR reaction utilizes at least one forward primer and a reverse primer. FIG. 3 shows examples of various primer pairings. For example, the forward primer can be an intracellular ALK primer (primer 100) 5'ACTACTGCTTTGCTGGCAAGACCT (SEQ ID NO: 7); an extra cellular EML4-ALK fusion primer (primer 103) 5'TGTTCAAGATCGCCTGTCAGCTCT (SEQ ID NO: 8); an extracellular NPM-ALK fusion primer (primer 102); 5'TCTGTACAGCCAACGGTTTCCCTT (SEQ ID NO: 9);

an extracellular CTLC-ALK fusion primer (primer 105) 5'GAGAGTGCTTTGGAGCTTGTCTGT (SEQ ID NO: 10); or an extracellular region of wildtype ALK primer from a region of non-homology (primer 104) 5' TTCCTTCATCA-GTCCACTGGGCAT (SEQ ID NO: 11). The reverse primer can be primer 101: 5' TCGTCCTGTTCAGAGCACACT-TCA (SEQ ID NO: 6). The RT-PCR reaction results in amplification products (i.e., amplicons) of the sizes shown in Table 3.

TABLE 3

| Primer Pair | PCR Product | Amplicon Size (bp) |
|---|---|---|
| 104/101 | Wt (Intra and Extra) | 615 |
| 100/101 | Wt (Intra Only) | 200 |
| 103/101 | EML4-ALK v1 | 1740 |
| 103/101 | EML4-ALK v2 | 2500 |
| 103/101 | EML4-ALK v3a | 920 |
| 103/101 | EML4-ALK v3b | 955 |
| 103/101 | EML4-ALK v4 | 2490 |
| 103/101 | EML4-ALK v5a | 691 |
| 103/101 | EML4-ALK v5b | 577 |
| 102/101 | NPM-ALK | 410 |
| 105/101 | CLTC-ALK | 529 |

B. Example 2

Microarray Design and Fabrication

Herein described is the development of a microarray diagnostic for the identification of specific ALK mutations. Herein disclosed is the fabrication of a DNA microarray composed of 47 unique elements that are capable of detecting 12 possible mutations and wildtype ALK as an internal control. Two scenarios to empirically can be pursued to optimize the input nucleic acid probe, involving reverse transcription, or reverse transcription and PCR (RT-PCR). In vitro feasibility based on the accurate detection of subcloned ALK fusions and variants can be demonstrated from plasmid constructs, and using various mutant ALK fusion-containing human cancer cell lines intermixed in a range of ratios with cell lines that contain wild-type ALK. ALK mutations can be identified from lung cancer biopsy specimens. This work can include benchmarking comparison studies with the available diagnostic standards, an ALK FISH assay and anti-ALK immunohistochemistry (IHC).

1. Oligonucleotide Design

Figure 4:
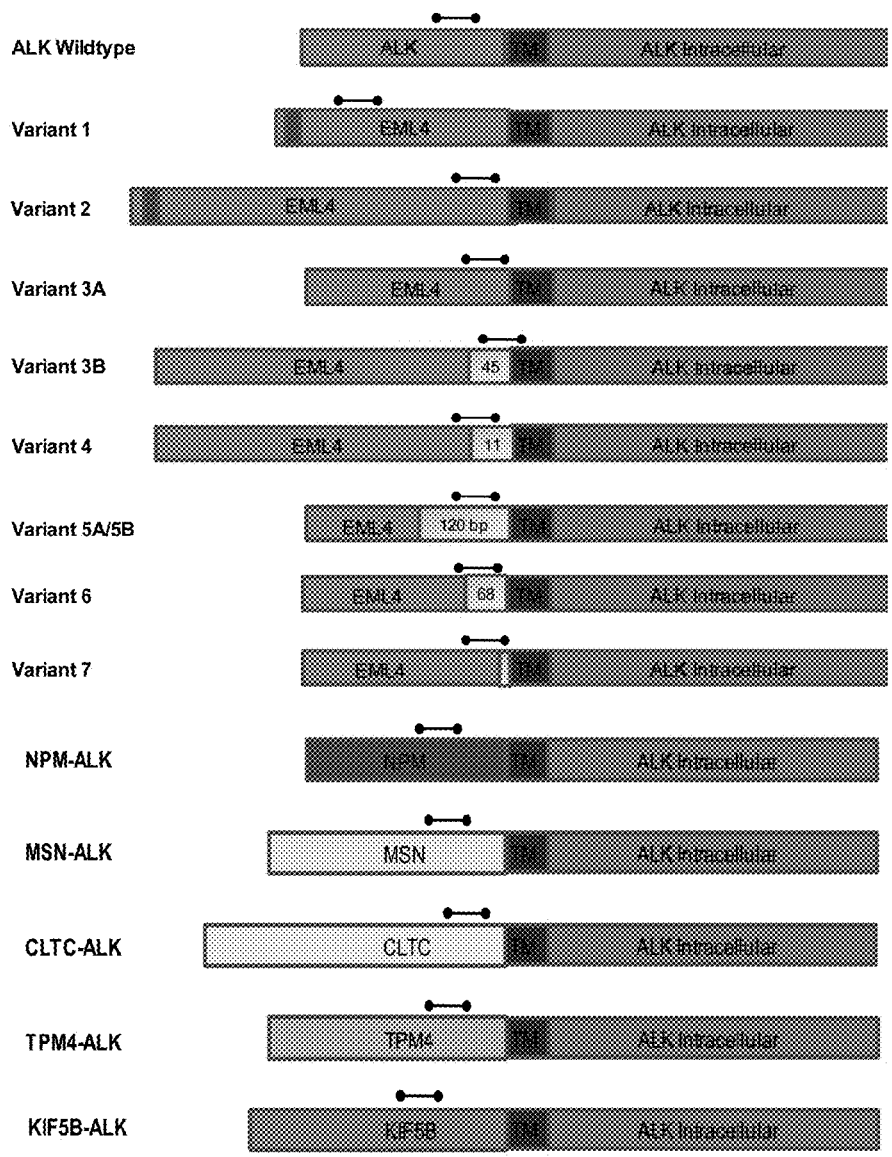
FIG. 4 shows approximate probe position and breakage region of wildtype ALK and various fusion partners including seven variants of EML4-ALK, NPM-ALK, MSN-ALK, CLTC-ALK, TPM-ALK, and KIF5B-ALK.

A strategy to identify ALK mutations and their subvariants through the detection of unique 5' regions of ALK fusion partners was designed. In general, the strategy was predicated on reverse transcription and extension and/or amplification from a region within the 3' intracellular region of ALK mRNAs, across the junctional site, and into the 5' portion of the fusion partner. Generated cDNA or amplified DNA are post-labeled with a covalently linked fluoroprobe and serve as input to the microarray. Two probes complementary to different regions within the 5' region of the fusion partner or ALK cDNA, printed in triplicate, serves as the microarray capture DNA. The position of hybridization and signal detection identifies the presence of ALK and/or ALK mutations and their expression relative to a set of ten housekeeping, internal control transcripts (FIG. 4 and Table 4).

TABLE 4

| ID Number | Sequence Definition | Probe Sequence | TM (° C.) | ID Letter | Sequence Definition | Primers | TM (° C.) |
|---|---|---|---|---|---|---|---|
| 1 | EML4-ALK V1PRO | TGTGCTAAAGGCGGCT TTGGCTGATGTT (SEQ ID NO: 33) | 64.5 | A | ALK Kinase domain Reverse primer | GGTCTTGCCAGCAA AGCAGTAGTT (SEQ ID NO: 32) | 59.9 |
| 2 | CLTC-ALK | TCACTGAGAAAAGAA GAAGAACAAGCTACA GAGACACAACCCA (SEQ ID NO: 34) | 65.1 | B | Extracellular region of ALK Forward | TCGGTTCTAGGGCT AAACGGCAAT (SEQ ID NO: 61) | 60.4 |
| 3 | EML4-ALK V2 | TACATCACACACCTTG ACTGGTCCCCAGACAA CAAGTAT (SEQ ID NO: 35) | 65.7 | C | EML4-ALK Variant 2 Forward | AGCAGATATGGAAG GTGCACTGGA (SEQ ID NO: 62) | 60.1 |
| 4 | EML4-ALK V2-2 | TATTGTACTTGTACCG CCGGAAGCACCAG (SEQ ID NO: 36) | 63.1 | D | EML4-ALK Variant 3A Forward | TCTCAAGTAAAGTG TACCGCCGGA (SEQ ID NO: 63) | 59.7 |
| 5 | EML4-ALK V3A | TGTGCTAAAGGCGGCT TTGGCTGATGTT (SEQ ID NO: 37) | 64.2 | E | EML4-ALK Variant 3B Forward | ACCTCGACCATCAT GACCGACTACAA (SEQ ID NO: 64) | 61.1 |
| 6 | EML4-ALK V3A-2 | AATCACTGTGCTAAAG GCGGCTTTGGCT (SEQ ID NO: 38) | 64.1 | F | EML4-ALK Variant 4 Forward | AGATATGCTGGATG AGCCCTGAGT (SEQ ID NO: 65) | 59.6 |
| 7 | EML4-ALK V3B | AAACAGCCAAGTGTA CCGCCGGAAG (SEQ ID NO: 39) | 63.2 | G | EML4-ALK Variant 5B Forward | GAAGTGGCCTGTGT AGTGCTTCAA (SEQ ID NO: 67) | 59.4 |
| 8 | EML4-ALK V4 | TATGCTGGATGAGCCC TGAGTACAAGCTGA (SEQ ID NO: 40) | 63.5 | H | EML4-ALK Variant 6 Forward | AAAGGAAGTGGCCT GTGTAGTGCT (SEQ ID NO: 68) | 60.6 |

TABLE 4-continued

| ID Number | Sequence Definition | Probe Sequence | TM (° C.) | ID Letter | Sequence Definition | Primers | TM (° C.) |
|---|---|---|---|---|---|---|---|
| 9 | EML4-ALK V4-2 | AGAGATATGCTGGAT GAGCCCTGAGT (SEQ ID NO: 41) | 60.6 | I | EML4-ALK Variant 7 Forward | AGAAATAGAGCACC AGGAGCTGCAAG (SEQ ID NO: 69) | 60.6 |
| 10 | EML4-ALK V5B | GGAGGATATGGAGAT CCAGGGAGGCTTCCTG TAGGAA (SEQ ID NO: 42) | 66.7 | J | NPM-ALK Forward | GCAGAGGCAATGAA TTACGAAGGC (SEQ ID NO: 70) | 70.2 |
| 11 | EML4-ALK V5B-2 | TGTGTAGTGCTTCAAG GGCCAGGCT (SEQ ID NO: 43) | 64.1 | K | KIF5B-ALK Forward | TGCATCTCGTGATC GCAAACGCTA (SEQ ID NO: 97) | 60.9 |
| 12 | EML4-ALk V6 | TGTGTAGTGCTTCAAG GGCCAGGCT (SEQ ID NO: 44) | 64.1 | L | TMP4-ALK Forward | AAACTGAAAGAGGC TGAGACCCGT (SEQ ID NO: 71) | 60.3 |
| 13 | EML4-ALk V6-2 | TGGGAAAGGACCTAA AGGAAGTGGCCTGT (SEQ ID NO: 45) | 64.2 | M | MSN-ALK Forward | TCAGGAACAGCTGG CCTTGGAAAT (SEQ ID NO: 72) | 61.0 |
| 14 | EML4-ALK V7 | CTGAAAGAGAAATAG AGCACCAGGAGCTGC AAGCCAT (SEQ ID NO: 48) | 65.8 | N | CLTC-ALK Forward | TTGTTTATGTGTACC GCCGGAAGC (SEQ ID NO: 73) | 59.8 |
| 15 | EML4-ALK V7-2 | AGAAATAGAGCACCA GGAGCTGCAAGCCAT (SEQ ID NO: 49) | 64.4 | O | ALK kinase domain forward primer | TGTACCGCCGGAAG CACCAGGAG (SEQ ID NO: 74) | 65.3 |
| 16 | KIF5B-ALK | CTATCAGCAAGAAGT AGATCGCATAAGGA AGCAGTCAGGTCA (SEQ ID NO: 50) | 65.0 | | ALK Kinase domain Reverse primer | TTGCTCAGCTTGTA CTCAGGGCT (SEQ ID NO: 46) | 60.5 |
| 17 | KIF5B-ALK 2 | ATGGCCAGAAGAGGG CATTCTGCACAGATT (SEQ ID NO: 51) | 64.7 | | ALK Kinase domain Reverse primer | AGGGCTTCCATGAG GAAATCCAGT (SEQ ID NO: 47) | 60.2 |
| 18 | MSN-ALK | TGACAGCTCGAATCTC CCAGCTGGAGAT (SEQ ID NO: 52) | 63.9 | | ALK kinase domain forward primer | TGTACCGCCGGAAG CACCAGGAG (SEQ ID NO: 75) | 65.3 |
| 19 | MSN-ALK 2 | TGGCCTTGGAAATGGC AGAGCTGACA (SEQ ID NO: 53) | 64.2 | | Tube 4 Primer F2 (Var 3A) | GATGAAATCACTGT GCTAAAGGCGGC (SEQ ID NO: 76) | 72.5 |
| 20 | TMP4-ALK | CGTGCTGAATTTGCAG AGAGAACGGTTGCA (SEQ ID NO: 54) | 64.0 | | Tube 4 Primer F3 (Var 3B) | GCAGACAAGCATAA AGATGTCATCATC (SEQ ID NO: 77) | 56.3 |
| 21 | TMP4-ALK 2 | AAAGAGGCTGAGACC CGTGCTGAATTTGCA (SEQ ID NO: 55) | 64.8 | | Tube 4 Primer F4 (Var 6) | CCACACCTGGGAAA GGACCTAAAGG (SEQ ID NO: 78) | 61.1 |
| 22 | NPM-ALK | AATGTCTGTACAGCCA ACGGTTTCCCTTGG (SEQ ID NO: 56) | 63.5 | | Tube 4 Primer F8 (CLTC) | TGCCATGCCCTATTT CATCCAGGT (SEQ ID NO: 79) | 59.8 |
| 23 | NPM-ALK 2 | AAGGTTGAAGTGTGGT TCAGGGCCAGT (SEQ ID NO: 59) | 63.7 | | Tube 4 Primer F9 (NPM) | GCAGAGGCAATGAA TTACGAAGGC (SEQ ID NO: 80) | 70.2 |
| 24 | Extracellular region of ALK Forward | ATGTCACATGGACCCT GAAAGCCACAAGGT (SEQ ID NO: 60) | 64.6 | | Extracellular region of ALK Forward | ACCCTGAAAGCCAC AAGGTCATCT (SEQ ID NO: 81) | 69.7 |

TABLE 4-continued

| ID Number | Sequence Definition | Probe Sequence | TM (° C.) | ID Letter | Sequence Definition | Primers | TM (° C.) |
|---|---|---|---|---|---|---|---|
| 25 | ALK Kinase domain Reverse primer | TCGTCCTGTTCAGAGC ACACTTCA (SEQ ID NO: 57) | 60.1 | | Extracellular region of ALK Forward | ACGCAATGGCTTCA AGGTTAC (SEQ ID NO: 82) | 55.4 |
| | | | | | Tube 6 primer R (Cox5B) | CGCTGGTATTGTCC TCTTCAC (SEQ ID NO: 83) | 54.7 |
| | | | | | ALK Kinase domain Reverse primer | AGGTCTTGCCAGCA AAGCAGTAGTT (SEQ ID NO: 58) | 59.9 |

| Sequence Definition | Probe Sequence | Sequence Definition | Primers |
|---|---|---|---|
| Wildtype | AGGATGGCGTCTCCTGCATTGTG TCA (SEQ ID NO: 84) | Extracellular region of ALK Forward | CTGAAAGCCACAAGGTCATCT GCT (SEQ ID NO: 89) |
| 3'Break | TGTATGAAGGCCAGGTGTCCGGA AT (SEQ ID NO: 85) | ALK Kinase domain Reverse primer | CAATCATGATGCCGGAGAAAG CCA (SEQ ID NO: 66) |
| Cox 5B | TCAGGCACCAGGGAAGACCCTA ATTT (SEQ ID NO: 86) | ALK kinase domain forward | AACTACTGCTTTGCTGGCAAGA CCTC (SEQ ID NO: 90) |
| ADAR | AACTCAGACCCAGGTTTGGAACC TGA (SEQ ID NO: 87) | ALK Kinase domain Reverse primer | TCGTCCTGTTCAGAGCACACTT CA (SEQ ID NO: 91) |
| EIF4A2 | TCCTTCGTGGCATCTATGCTTAC GGT (SEQ ID NO: 88) | Cox 5B forward | TGCAAAGAAGGGACTGGACCC ATA (SEQ ID NO: 92) |
| | | Cox 5B reverse | TTGTCCTCTTCACAGATGCAGC CT (SEQ ID NO: 93) |
| | | ADAR forward | AGACCAGACAGTCATAGCCAA GGA (SEQ ID NO: 94) |
| | | ADAR reverse | AAGGCAGATGTGGAGTTGCTG TCT (SEQ ID NO: 95) |
| | | EIF4A2 forward | TATAACAGAGAACATGGCGGC CCA (SEQ ID NO: 96) |

Each synthesized probe was optimized to a melting temperature of 65° C. and a unique hybridization region within the 5' fusion partner or ALK using the program OLIGO-ANLYZER 3.1®. The melting temperature and approximate length of 30 nucleotides were selected based on reports of optimized microarray conditions. A 5' monomethoxytrityl C-6 amino linker has been added to the probes to enable their purification and conjugation to prepared glass slides. This linker was selected based on chemistry optimization. Lastly, two probes for each ALK fusion partner, ideally at different regions of the fusion partner, were synthesized to provide an alternative method of identification in the event that a probe was prevented from binding to a region by a conformational restriction of tertiary DNA structure. These criteria were also applied to the design of the internal controls.

PCR Primers

Each synthesized primer was again optimized to a theoretical melting temperature of 60° C. and unique regions of within both the 5' fusion partner and 3' ALK intracellular domain using the program OLIGOANLYZER 3.1®. The primer defined as "Universal ALK Reverse Primer" serve as a common primer for the reverse transcription step. The other listed primers permit for subsequent PCR steps and amplification of putative targets. These criteria were also applied to the design of the internal controls.

Optimization of RT-PCR Primers

Primers for RT-PCR have been optimized to a binding Tm of 60° C. for the generation of putative target DNA. These primers have been optimized as single amplicon reactions; however, several or all can be batched to allow multiplexing of putative target DNA. PCR amplification protocol utilized 35 cycles with 95° C. for 15 min; 94° C. for 30s; 52° C. for 1 min; 72° C. for 1 min; 72° C. for 15 min, and 4° C.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Throughout the description and claims of this specification, the word "comprise" and variations of the word, such as "comprising" and "comprises," means "including but not limited to," and is not intended to exclude, for example, other additives, components, integers or steps.

Those skilled in the art will recognize, or be able to ascertain using no more than routine experimentation, many equivalents to the specific embodiments of the method and compositions described herein. Such equivalents are intended to be encompassed by the following claims.

REFERENCES

Babon J J, McKenzie M, Cotton R G. Mutation detection using fluorescent enzyme mismatch cleavage with T4 endonuclease VII. Electrophoresis 1999; 20(6):1162-70.

Brow M A, Oldenburg M C, Lyamichev V, et al. Differentiation of bacterial 16S rRNA genes and intergenic regions and *Mycobacterium tuberculosis* katG genes by structure-specific endonuclease cleavage. J Clin Microbiol 1996; 34(12):3129-37.

Chen T J, Boles R G, Wong L J. Detection of mitochondrial DNA mutations by temporal temperature gradient gel electrophoresis. Clin Chem 1999; 45(8 Pt 1):1162-7.

Cotton R G, Rodrigues N R, Campbell R D. Reactivity of cytosine and thymine in single-base-pair mismatches with hydroxylamine and osmium tetroxide and its application to the study of mutations. Proc Natl Acad Sci USA 1988; 85(12):4397-401.

Fodde R, Losekoot M. Mutation detection by denaturing gradient gel electrophoresis (DGGE). Hum Mutat 1994; 3(2):83-94.

Ganguly A, Prockop D J. Detection of mismatched bases in double stranded DNA by gel electrophoresis. Electrophoresis 1995; 16(10):1830-5.

Ganguly A, Rock M J, Prockop D J. Conformation-sensitive gel electrophoresis for rapid detection of single-base differences in double-stranded PCR products and DNA fragments: evidence for solvent-induced bends in DNA heteroduplexes. Proc Natl Acad Sci USA 1993; 90(21):10325-9.

Gleason B C, Hornick J L. J Clin Pathol 2008 April; 61(4):428-37.

Hacia J G. Resequencing and mutational analysis using oligonucleotide microarrays. Nat Genet 1999; 21(1 Suppl):42-7.

Hovig E, Smith-Sorensen B, Brogger A, Borresen A L. Constant denaturant gel electrophoresis, a modification of denaturing gradient gel electrophoresis, in mutation detection. Mutat Res 1991; 262(1):63-71.

Labeit S, Lehrach H, Goody R S. A new method of DNA sequencing using deoxynucleoside alpha-thiotriphosphates. Dna 1986; 5(2):173-7.

Labeit S, Lehrach H, Goody R S. DNA sequencing using alpha-thiodeoxynucleotides. Methods Enzymol 1987; 155:166-77.

Lamant L et al., Genes Chromosomes Cancer. 2003 August; 37(4):427-32

Li R, Morris S W., Med Res Rev. 2008 May; 28(3):372-412.

Lu A L, Hsu I C. Detection of single DNA base mutations with mismatch repair enzymes. Genomics 1992; 14(2):249-55.

Mano H., Cancer Sci. 2008 December; 99(12):2349-55

Myers R M, Larin Z, Maniatis T. Detection of single base substitutions by ribonuclease cleavage at mismatches in RNA:DNA duplexes. Science 1985; 230(4731):1242-6.

Nagamine C M, Chan K, Lau Y F. A PCR artifact: generation of heteroduplexes. Am J Hum Genet 1989; 45(2):337-9.

Nakamaye K L, Gish G, Eckstein F, Vosberg H P. Direct sequencing of polymerase chain reaction amplified DNA fragments through the incorporation of deoxynucleoside alpha-thiotriphosphates. Nucleic Acids Res 1988; 16(21):9947-59.

Novack D F, Casna N J, Fischer S G, Ford J P. Detection of single base-pair mismatches in DNA by chemical modification followed by electrophoresis in 15% polyacrylamide gel. Proc Natl Acad Sci USA 1986; 83(3):586-90.

Oldenburg M C, Siebert M. New Cleavase Fragment Length Polymorphism method improves the mutation detection assay. Biotechniques 2000; 28(2):351-7.

Orita M, Suzuki Y, Sekiya T, Hayashi K. Rapid and sensitive detection of point mutations and DNA polymorphisms using the polymerase chain reaction. Genomics 1989; 5(4):874-9.

Pincas H, Pingle M R, Huang J, et al. High sensitivity EndoV mutation scanning through real-time ligase proofreading. Nucleic Acids Res 2004; 32(19):e148.

Porter K W, Briley J D, Shaw B R. Direct PCR sequencing with boronated nucleotides. Nucleic Acids Res 1997; 25(8):1611-7.

Rudzki Z et al., Pol J Pathol. 2005; 56(1):37-45

Takeuchi K et al., Clin Cancer Res. 2009 May 1; 15(9):3143-9

Winter E, Yamamoto F, Almoguera C, Perucho M. A method to detect and characterize point mutations in transcribed genes: amplification and overexpression of the mutant c-Ki-ras allele in human tumor cells. Proc Natl Acad Sci USA 1985; 82(22):7575-9.

Xiao W, Oefner P J. Denaturing high-performance liquid chromatography: A review. Hum Mutat 2001; 17(6):439-74.

Youil R, Kemper B, Cotton R G. Detection of 81 of 81 known mouse beta-globin promoter mutations with T4 endonuclease VII—the EMC method. Genomics 1996; 32:431-5.

---

SEQUENCES
SEQ ID NO: 1 anaplastic lymphoma kinase (ALK)

```
  1   mgaigllwll plllstaavg sgmgtgqrag spaagpplqp replsysrlq rkslavdfvv 61   pslfrvyard lllppsssel kagrpeargs laldcapllr llgpapgvsw tagspapaea 121   rtlsrvlkgg svrklrrakq lvlelgeeai legcvgppge aavgllqfnl selfswwirq
```

-continued

| SEQUENCES |
|---|
| SEQ ID NO: 1 anaplastic lymphoma kinase (ALK) |

```
 181   gegrlrirlm pekkasevgr egrlsaaira sqprllfqif gtghsslesp tnmpspspdy
 241   ftwnltwimk dsfpflshrs ryglecsfdf pceleysppl hdlrnqswsw rripseeasq
 301   mdlldgpgae rskemprgsf lllntsadsk htilspwmrs ssehctlavs vhrhlqpsgr
 361   yiaqllphne aareillmpt pgkhgwtvlq grigrpdnpf rvaleyissg nrslsavdff
 421   alkncsegts pgskmalqss ftcwngtvlq lgqacdfhqd caqgedesqm crklpvgfyc
 481   nfedgfcgwt qgtlsphtpq wqvrtlkdar fqdhqdhall lsttdvpase satvtsatfp
 541   apiksspcel rmswlirgvl rgnvslvlve nktgkeqgrm vwhvaayegl slwqwmvlpl
 601   ldvsdrfwlq mvawwgqgsr aivafdnisi sldcyltisg edkilqntap ksrnlfernp
 661   nkelkpgens prqtpifdpt vhwlfttcga sgphgptqaq cnnayqnsnl svevgsegpl
 721   kgiqiwkvpa tdtysisgyg aaggkggknt mmrshgvsvl gifnlekddm lyilvgqqge
 781   dacpstnqli qkvcigennv ieeeirvnrs vhewagggggg gggatyvfkm kdgvpvplii
 841   aaggggrayg aktdtfhper lennssvlgl ngnsgaaggg ggwndntsll wagkslqega
 901   tgghscpqam kkwgwetrgg fgggggggcss gggggyigg naasnndpem dgedgvsfis
 961   plgilytpal kvmeghgevn ikhylncshc evdechmdpe shkvicfcdh gtvlaedgvs
1021   civsptpeph lplslilsvv tsalvaalvl afsgimivyr rkhqelqamq melqspeykl
1081   sklrtstimt dynpnycfag ktssisdlke vprknitlir glghgafgev yegqvsgmpn
1141   dpsplqvavk tlpevcseqd eldflmeali iskfnhqniv rcigvslqsl prfillelma
1201   ggdlksflre trprpsqpss lamldllhva rdiacgcqyl eenhfihrdi aarnclltcp
1261   gpgrvakigd fgmardiyra syyrkggcam lpvkwmppea fmegiftskt dtwsfgvllw
1321   eifslgympy psksnqevle fvtsggrmdp pkncpgpvyr imtqcwqhqp edrpnfaiil
1381   erieyctqdp dvintalpie ygplveeeek vpvrpkdpeg vppllvsqqa kreeerspaa
1441   ppplpttssg kaakkptaae isvrvprgpa vegghvnmaf sqsnppselh kvhgsrnkpt
1501   slwnptygsw ftekptkknn piakkephdr gnlglegsct vppnvatgrl pgaslleps
1561   sltanmkevp lfrlrhfpcg nvnygyqqqg lpleaatapg aghyedtilk sknsmnqpgp
```

What is claimed is:

1. A kit for diagnosing a cancer comprising an anaplastic lymphoma kinase (ALK) fusion or oncogenic ALK transcript the kit comprising at least one forward and reverse primer pair that specifically hybridizes to an ALK kinase domain as set forth in SEQ ID NO: 1, wherein at least one forward primer is SEQ ID NO:3 and at least one reverse primer is SEQ ID NO:2, and wherein at least one primer is a scorpion primer.

2. The kit of claim 1, wherein the reverse primer is a scorpion primer.

3. The kit of claim 2, wherein the reverse primer is a uni-molecular scorpion probe and primer.

4. The kit of claim 1 further comprising a second forward and reverse primer.

5. The kit of claim 4, wherein the second forward and reverse primers specifically hybridize to extracellular region ALK.

6. The kit of claim 1, further comprising a control forward and reverse primer pair.

7. The kit of claim 6, wherein the control primer pair specifically hybridizes to ABL1 mRNA.

8. The kit of claim 7, wherein the control forward and reverse primer pair comprise SEQ ID NO: 4 and SEQ ID NO: 5.

* * * * *